US012202832B2

(12) United States Patent
Kitamura et al.

(10) Patent No.: US 12,202,832 B2
(45) Date of Patent: Jan. 21, 2025

(54) HETEROCYCLIC COMPOUNDS HAVING A CALCIUM-SENSING RECEPTOR ANTAGONISTIC ACTIVITY

(71) Applicant: TAKEDA PHARMACEUTICAL COMPANY LIMITED, Osaka (JP)

(72) Inventors: Shuji Kitamura, Kanagawa (JP); Zenichi Ikeda, Kanagawa (JP); Minoru Ikoma, Kanagawa (JP); Koji Watanabe, Kanagawa (JP); Hideki Hirose, Kanagawa (JP); Takafumi Yukawa, Kanagawa (JP); Sachie Morimoto, Kanagawa (JP); Naoki Nishizawa, Kanagawa (JP); Taiji Asami, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 1251 days.

(21) Appl. No.: 16/608,723

(22) PCT Filed: Apr. 26, 2018

(86) PCT No.: PCT/JP2018/016996
§ 371 (c)(1),
(2) Date: Oct. 25, 2020

(87) PCT Pub. No.: WO2018/199236
PCT Pub. Date: Nov. 1, 2018

(65) Prior Publication Data
US 2021/0115048 A1    Apr. 22, 2021

(30) Foreign Application Priority Data
Apr. 27, 2017   (JP) ................. 2017-087950

(51) Int. Cl.
*C07D 487/04* (2006.01)
*A61K 9/20* (2006.01)
*A61K 9/48* (2006.01)
*A61K 31/4184* (2006.01)
*A61K 47/38* (2006.01)
*A61P 9/04* (2006.01)

(52) U.S. Cl.
CPC .......... *C07D 487/04* (2013.01); *A61K 9/2013* (2013.01); *A61K 9/2018* (2013.01); *A61K 9/2054* (2013.01); *A61K 9/2059* (2013.01); *A61K 9/4858* (2013.01); *A61K 9/4866* (2013.01); *A61K 31/4184* (2013.01); *A61K 47/38* (2013.01); *A61P 9/04* (2018.01)

(58) Field of Classification Search
CPC .. C07D 487/04; A61K 9/2013; A61K 9/2018; A61K 9/2054; A61K 9/2059; A61K 9/4858; A61K 9/4866; A61K 31/4184; A61K 47/38; A61K 31/519; A61K 2300/00; A61P 9/04; A61P 9/12; A61P 11/00

USPC ......................................................... 514/259
See application file for complete search history.

(56) References Cited

U.S. PATENT DOCUMENTS

| 7,514,441 | B2* | 4/2009 | Yasuma ................. A61P 43/00 544/263 |
|---|---|---|---|
| 9,447,100 | B2 | 9/2016 | Yasuma et al. |
| 2004/0127508 | A1 | 7/2004 | Gerlach et al. |
| 2004/0242602 | A1 | 12/2004 | Gungor et al. |
| 2006/0079536 | A1 | 4/2006 | Yasuma et al. |
| 2006/0111348 | A1 | 5/2006 | Kampen et al. |
| 2009/0304821 | A1 | 12/2009 | Notoya et al. |
| 2010/0273753 | A1 | 10/2010 | Li |
| 2015/0266872 | A1* | 9/2015 | Koike .................. C07D 413/04 548/312.1 |
| 2016/0060267 | A1 | 3/2016 | Albrecht et al. |

FOREIGN PATENT DOCUMENTS

| CA | 3009609 A1 | 6/2017 |
|---|---|---|
| CN | 1045973 A | 10/1990 |
| CN | 1771231 A | 5/2006 |
| CN | 101969774 A | 2/2011 |
| CN | 104910118 A | 9/2015 |
| EP | 0390112 A2 | 10/1990 |
| EP | 3395344 A1 | 10/2018 |
| EP | 3437644 A1 | 2/2019 |
| JP | 2005239611 A * | 9/2005 |

(Continued)

OTHER PUBLICATIONS

Lu et al. Cellular Physiology and Biochemistry, 2013, 31:728-743, "Role of the Calcium-Sensing Receptor in Cardiomyocyte Apoptosis via the Sarcoplasmic Reticulum and Mitochondrial Death Pathway in Cardiac Hypertrophy and Heart Failure". (Year: 2013).*
Circulation Research, 2012, 111(4):469-481, "Enhanced Ca2+-Sensing Receptor Function in Idiopathic Pulmonary Arterial Hypertension". (Year: 2012).*
Yoshida et al. Bioorganic & Medicinal Chemistry 19, 2011, 1881-1894. (Year: 2011).*
United States Patent Office Action for U.S. Appl. No. 16/089,533 dated Dec. 14, 2020 (9 pages).
Gehlbach et al., "The Pulmonary Manifestations of Left Heart Failure," Chest, 2004, 125(2): 669-682.

(Continued)

*Primary Examiner* — Jared Barsky
*Assistant Examiner* — Liyuan Mou
(74) *Attorney, Agent, or Firm* — Michael Best & Friedrich LLP

(57) ABSTRACT

The present invention provides a compound or a salt thereof having a calcium-sensing receptor antagonistic activity, and being expected to be useful as an agent for preventing or treating heart failure, pulmonary hypertension, or the like. The compounds represented by formula (I) or a salt thereof has a calcium-sensing receptor antagonistic activity, and is expected to be useful as an agent for preventing or treating heart failure, pulmonary hypertension, or the like, wherein each symbol is as described in the specification.

7 Claims, 3 Drawing Sheets

(56) References Cited

FOREIGN PATENT DOCUMENTS

| JP | 2006510582 A | 3/2006 |
|---|---|---|
| RU | 2003129060 A | 4/2005 |
| RU | 2015143517 A | 9/2014 |
| WO | 2004017908 A2 | 3/2004 |
| WO | 2009155448 A1 | 12/2009 |
| WO | 2013113860 A1 | 8/2013 |
| WO | 2014061676 A1 | 4/2014 |
| WO | 2017110881 A1 | 6/2017 |
| WO | 2017170354 A1 | 10/2017 |

OTHER PUBLICATIONS

Dunlap et al., "Pulmonary Hypertension: Diagnosis and Treatment," Am Fam Physician, 2016, 94(6): 463-469.
Korman et al., "Elevated Adipsin Levels are Associated with Pulmonary Arterial Hypertension in Systemic Sclerosis," Arthritis Rheumatol, 2017, 69(10): 2062-2068.
Yoshida et al., "Novel and potent calcium-sensing receptor antagonists: Discovery of (5R)-N-[1-ethyl-1-4(4-ethylphenyl0propyl]-2,7,7-trimethyl-5-phenyl-4,5,6,7-tetrahydropyrazolo[1,5-a]pyrimidine-3-carboxamide monotosylate (TAK-075) as an orally active bone anabolic agent," Bioorganic & Medicinal Chemistry, 2011, 19:1881-1894.
Zaruba et al., "Parathyroid hormone treatment after myocardial infarction promotes cardiac repair by enhanced neovascularization and cell survival," Cardiovascular Research, 2008, 77:722-731.
Brunner et al., "The cardioprotective effects of parathyroid hormone are independent of endogenous granulocyte-colony stimulating factor release," Cardiovascular Research, 2012, 93:330-339.
Cha et al., "Parathyroid hormone accelerates decompensation following left ventricular hypertrophy," Experimental and Molecular Medicine, 2010, 42(1):61-68.
Liu et al., "Calhex231 Ameliorates Cardiac Hypertrophy by Inhibiting Cellular Autophagy in Vivo and in Vitro," Cellular Physiology and Biochemistry, 2015, 36:1597-1612.
Zhang et al., "Calcium Sensing Receptor Promotes Cardiac Fibroblast Proliferation and Extracellular Matrix Secretion," Cellular Physiology and Biochemistry, 2014, 33:557-568.
Sun et al., "Calcium-sensing receptor: a sensor and mediator of ischemic preconditioning in the heart," Am J Physiol Heart Circ Physiol, 2010, 299:H1309-H1317.
Yamamura, "Pathological function of Ca2+-sensing receptor in pulmonary arterial hypertension," J. Smooth Muscle Res., 2014, 50:8-17.
Lu et al., "Role of the Calcium-Sensing Receptor in Cardiomyocyte Apoptosis via the Sarcoplasmic Reticulum and Mitochondrial Death Pathway in Cardiac Hypertrophy and Heart Failure," Cellular Physiology and Biochemistry, 2013, 31:728-743.
Li et al., "Role of Calcium-Sensing Receptor in Cardiac Injury of Hereditary Epileptic Rats," Pharmacology, 2015, 95:10-21.
Tfelt-Hansen et al., "Calcium receptor is functionally expressed in rat neonatal ventricular cardiomyocytes," Am J Physiol Heart Circ Physiol, 2006, 290:H1165-H1171.
Liu et al., "Rat Parathyroid Hormone 1—34 Signals through the MEK/ERK Pathway to Induce Cardiac Hypertrophy," The Journal of International Medical Research, 2008, 36:942-950.
Smogorzewski et al., "Parathyroid hormone increases cytosolic calcium concentration in adult rat cardiac myocytes," Am J Physiol Heart Circ Physiol, 1993, 264:H1998-H2006.
Tastan et al., "Parathyroid hormone improves contractile performance of adult rat ventricular cardiomyocytes at low concentrations in a non-acute way," Cardiovascular Research, 2009, 82:77-83.
Yamamura et al., "Enhanced Ca2+-Sensing Receptor Function in Idiopathic Pulmonary Arterial Hypertension," Circ Ress, 2012, 111(4):469-481.
Yamamura et al., "Dihydropyridine Ca2+ Channel Blockers Increase Cytosolic [Ca2+] by Activating Ca2+-sensing Receptors in Pulmonary Arterial Smooth Muscle Cells," Circ Res, 2013, 112(4):640-650.
Yamamura et al., "Enhanced Ca2+-sensing Receptor Function in Pulmonary Hypertension," The Pharmaceutical Society of Japan, 2013, 133(12):1351-1359.
Guo et al., "Inhibition of the Ca2+-sensing receptor rescues pulmonary hypertension in rats and mice," Hypertension Research, 2014, 37:116-124.
Yamamura et al., "Calcilytics enhance sildenafil-induced antiproliferation in idiopathic pulmonary arterial hypertension," European Journal of Pharmacology, 2016, 784:15-21.
Tang et al., "Pathogenic role of calcium-sensing receptors in the development and progression of pulmonary hypertension," Am J Physiol Lung Cell Mol Physiol, 2016, 310:L846-L859.
Schepelmann et al., "The vascular Ca2+-sensing receptor regulates blood vessel tone and blood pressure," Am J Physiol Cell Physiol, 2016, 310:C193-C204.
Yoshida et al., "Synthesis and structure-activity relationship of tetrahydropyrazolopyrimidine derivates—A novel structural class of potent calcium-sensing receptor," Bioorganic & Medical Chemistry, 2010, 18:8501-8511.
Yoshida et al., "Discovery of Novel and Potent Orally Active Calcium-Sensing Receptor Antagonist that Stimulate Pulselike Parathyroid Hormone Secretion: Synthesis and Structure—Activity Relationships of Tetrahydropyrazolopyrimidine Derivates," Journal of Medicinal Chemistry, 2011, 54(5):1430-1440.
International Search Report for Application No. PCT/JP2016/088121 dated Mar. 14, 2017 (5 pages, English translation included).
International Search Report for Application No. PCT/JP2017/012305 dated May 16, 2017 (5 pages, English translation Included).
Written Opinion for Application No. PCT/JP2017/012305 dated May 16, 2017 (8 pages, English translation only).
International Search Report for Application No. PCT/JP2018/016995 dated Jun. 12, 2018 (4 pages, English translation Included).
International Search Report for Application No. PCT/JP2018/016996 dated Jun. 19, 2018 (4 pages, English translation Included).
European Patent Office Extended Search Report for Application No. 16878768.7 dated Aug. 5, 2019 (8 pages).
Chinese Patent Office Action for Application No. 201680076074.0 dated Apr. 13, 2020 (14 pages, English translation Included).
Republic of Colombia Colombian Patent Office Action for Application No. 20190012270 dated Nov. 30, 2021 (10 pages including English translation).
European Patent Office Extended Search Report for counterpart application No. 17774891.0 dated Oct. 29, 2019 (7 pages).
Yamamura et al., "Inhibition of Excessive Cell Proliferation by Calcilytics in Idiopathic Pulmonary Arterial Hypertension," PLoS ONE, Sep. 2015, 10(9):e0138384 (15 pages).
Chinese Patent Office Action for Application No. 201880028226.9 dated Aug. 2, 2021 (8 pages including English summary).
Bastin et al., "Salt Selection and Optimisation Procedures for Pharmaceutical New Chemical Entities", Organic Process Research and Development, 2000, vol. 4, pp. 427-435.
Petrovskii, "Great Medical Encyclopedia vol. 12, Cryosurgery—Lenergre, Medicines", Third Publication, 1980, pp. 526-529 (27 pages, English translation included).
Belikov, "Part 1, General pharmaceutical chemistry", Pharmaceutical Chemistry Textbook, 2007, 18 pages including English translation.
Russian Patent Office Action for Application No. 2019138176 dated Jul. 16, 2021 (30 pages including English translation).
Russian Patent Office Action for Application No. 2019138175 dated Jun. 10, 2021 (30 pages including English translation).
Slivnick et al., "Hypertension and Heart Failure", Heart Failure Clinics, Oct. 2019, vol. 15, Iss. 4, (pp. 531-541).
Chinese Patent Office Invalidation Decision for Application No. 201580072874.0 dated Sep. 15, 2022 (26 pages including English translation).
CNIPA Case Analysis, dated Jul. 20, 2022 (4 pages including English translation).
Chinese Patent Office Action for Application No. 201680076074.0, dated Jul. 27, 2023, (22 pages including English summary).
Japanese Patent Office Notice of Reasons for Refusal for Application No. 2019-514620 dated May 17, 222 (4 pages including English translation).

(56) References Cited

OTHER PUBLICATIONS

Chinese Patent Office Action for Application No. 20188002818.5 dated Aug. 4, 2021 (18 pages including English translation).
Popovici-Muller et al., "Pyrazolo[1,5-a]pyrimidine-based inhibitors of HCV polymerase", Bioorganic & Medicinal Chemistry Letters, vol. 19, 2009, pp. 6331-6336.
Ma et al., "Chapter 14: Pulmonary Hypertension, Section 3: Treatment", in Modern Clinical Diagnosis and Treatment of Cardiovascular Diseases, First edition 2012, 9 pages including English translation.
Yu et al., "Internal Medicine Section of Traditional Chinese Medicine", Physician Assessment Training Standard Course, 2016, 9 pages including English translation.
Liang, "Studies on the Synthesis and Antimyocardial Ischemia Evaluation of the Ivabradine Analogues as Antianginal Agents", Masters dissertation to Dong Hua University, 2009, 78 pages including English translation of abstract.
Chen et al., "Attenuation of Compensatory Right Ventricular Hypertrophy and Heart Failure following Monocrotaline-Induced Pulmonary Vascular Injury by the Na+-H+ Exchange Inhibitor Cariporde", The Journal of Pharmacology and Experimental Therapeutics, 2001, vol. 298, No. 2, pp. 469-476.
Yu et al., "Deficiency of the NHE1 Gene Prevents Hypoxia-induced Pulmonary Hypertension and Vascular Remodeling", Am J Respir Crit Care Med, 2008, vol. 177, pp. 1276-1284.
Huetsch et al., "Na+/H+ exchange and hypoxic pulmonary hypertension", Pulmonary Circulation, 2015, vol. 5, No. 2, pp. 228-243.
United States Patent Office Notice of Allowance for U.S. Appl. No. 16/608,140 dated Sep. 11, 2020 (13 pages).
Gupta et al., "Animal Models for Heart Failure," Methods in Molecular Medicine, vol. 129: Cardiovascular Disease: Methods and Protocols, vol. 2: Molecular Medicine Edited by: Q. K. Wang, Humana Press Inc., Totowa, NJ, 2007, pp. 97-114.
Schreckenberg et al., "Calcium sensing receptor expression and signalling in cardiovascular physiology and disease," Vascular Pharmacology 107 (2018) 35-42.
Jones et al., "Regulation of Ca2+ signaling in transgenic mouse cardiac myocytes overexpressing calsequestrin," J Clin Invest. 1998, 101(7):1385-1393.

Wang et al., "Murine models for the study of congestive heart failure: Implications for understanding molecular mechanisms and for drug discovery," Journal of Pharmacological and Toxicological Methods 50 (2004) 163-174.
Chinese Patent Office Notification of Reexamination for Application No. 201680076074.0 dated Apr. 23, 2023 (12 pages including English translation).
Qian, "Pharmacology", China Medicine Science and Technology Press, 4th Edition, Aug. 2015, pp. 252-254.
Hara et al., "TAK-272 (imarikiren), a novel renin inhibitor, improves cardiac remodeling and mortality in a murine heart failure model", PLoS One, 2018, pp. 1-16.
Hara et al., "Development of a novel murine heart failure model overexpressing human renin and angiotensinogen", FEBS OpenBio, 2020, vol. 10, pp. 718-725.
Gerbino et al., "The Different Facets of Extracellular Calcium Sensors: Old and New Concepts in Calcium-Sensing Receptor Signalling and Pharmacology", International Journal of Molecular Sciences, 2018, vol. 19, No. 999, pp. 1-38.
Zhang et al., "Ischemic postconditioning and pinacidil suppress calcium overload in anoxia-reoxygenation cardiomyocytes via downregulation of the calcium-sensing receptor", PeerJ, 2016, 14 pages.
Bristow et al., "Structual and Functional Phenotyping of the Failing Heart: Is the Left Ventricular Ejection Fraction Obsolete?", JACC: Heart Failure, 2017, vol. 5, No. 11, pp. 772-781.
Shah et al., "Oxidative Stress as a Mechanism for Functional Alterations in Cardiac Hypertrophy and Heart Failure", Antioxidants, 2021, vol. 10, pp. 1-19.
Heger et al., "Molecular switches under TGFbeta signaling during progression from cardiac hypertrophy to heart failure", British Journal of Pharmacology, 2016, vol. 173, pp. 3-14.
Bai et al., "Decrease in calcium-sensing receptor in the progress of diabetic cardiomyopathy", Diabetes Research and Clinical Practice, 2012, col. 95, pp. 378-385.
Dyukova et al., "Influence of Ischemic Pre- and Post-Conditioning on Cardiac Expression of Calcium-Sensing Receptor", BioNanoSci., 2017, vol. 7, pp. 112-114.
Tham et al., "Pathophysiology of cardiac hypertrophy and heart failure: signaling pathways and novel therapeutic targets", Arch Toxicol., 2015, vol. 89, pp. 1401-1438.

\* cited by examiner

Table 5: Definitions and Classification of Cardiomyopathies (AHA proposal)

Primary cardiomyopathies (in which the clinically relevant disease processes predominantly involve the heart) are Circulation 2006; 113: 1807-1816

Table 6: Definitions and Classification of Cardiomyopathies (ESC proposal)

ARVC: Arrhythmogenic Right Ventricular Cardiomyopathy, DCM: Dilated Cardiomyopathy,
Eur Heart J 2008; 29: 270-276

HETEROCYCLIC COMPOUNDS HAVING A CALCIUM-SENSING RECEPTOR ANTAGONISTIC ACTIVITY

CROSS-REFERENCE TO RELATED APPLICATION(S)

This is a U.S. national stage entry of International Patent Application No. PCT/JP2018/016996, filed on Apr. 26, 2018, which claims priority to Japanese Patent Application No. 2017-087950, filed on Apr. 27, 2017, the entire contents of each of which are fully incorporated herein by reference.

TECHNICAL FIELD

The present invention relates to a heterocyclic compound having a calcium-sensing receptor antagonistic activity and being useful as an agent for preventing or treating heart failure, pulmonary hypertension, or the like.

BACKGROUND ART

Heart failure is a disease characterized by a condition that cardiac output is decreased due to cardiomyocytes dysfunction and a condition resulting from a burden on the body caused by cardiac output maintenance mechanisms. The function of cardiomyocytes is contraction and relaxation, and the contraction and relaxation require $Ca^{2+}$ ions. The contraction of cardiomyocytes is generated by the stage where the action potential is transmitted to the transverse tubule and the transverse tubular membrane is depolarized; the stage where $Ca^{2+}$ ions inflow from a voltage-dependent L-type $Ca^{2+}$ channel of the transverse tubule into the cell; and the stage where the flowed $Ca^{2+}$ ions bind to $Ca^{2+}$ release channels (ryanodine receptors or RYRs) of sarcoplasmic reticulum to release $Ca^{2+}$ ions from the sarcoplasmic reticulum to cytoplasm; and the stage where $Ca^{2+}$ ions released into cells bind to troponin C to induce contraction of cardiomyocytes. Furthermore, the relaxation of cardiomyocytes is generated by incorporation of $Ca^{2+}$ ions into sarcoplasmic reticulum through $Ca^{2+}$ release pumps (SERCA) which decrease cytoplasmic $Ca^{2+}$ ions and deviate $Ca^{2+}$ ions from troponin C. If an abnormality occurs in any of the stage above and $Ca^{2+}$ ions are not released into the cytoplasm, cardiomyocytes cause dysfunction to develop heart failure.

As the therapeutics for heart failure, for example, beta blockers, anti-aldosterone drugs, diuretics, digitalis, and cardiotonics are used in clinical settings to improve short-term symptoms and stabilize hemodynamics. However, these therapeutics are insufficient to improve the readmission rates or long-term prognosis. Thus, in recent years, new heart failure therapeutics which improve the readmission rates and long-term prognosis has been desired.

Pulmonary hypertension is a disease having a very poor prognosis, in which pulmonary arterial pressure increases due to abnormal proliferation, remodeling, and contraction of cardiac muscle or pulmonary vascular tissues, and as the disease progresses, right heart failure occurs, leading to death. The main therapeutics used for pulmonary hypertension include endothelin receptor antagonists, phosphodiesterase 5 inhibitors, prostacyclin analogues, soluble guanylate cyclase (sGC) stimulators. These therapeutics improve some symptoms, but the prognosis remains poor. In recent years, it has been found that multiple molecules are involved in the pathogenesis of this disease. Since the effects of the current therapeutics alone are limited, the development of new therapeutics has been desired.

Calcium-sensing receptors (CaSR) are G-protein coupled receptors (GPCR) which sense changes in extracellular calcium concentration, and are known to be associated with a variety of diseases.

Patent Literature 1 discloses heterocyclic compounds or salts thereof represented by the formulae below. This literature also describes that these compounds or salts thereof have a calcium-sensing receptor (CaSR) control action (agonist activity or antagonist activity) and secretion control actions of parathyroid hormone (PTH) thereby.

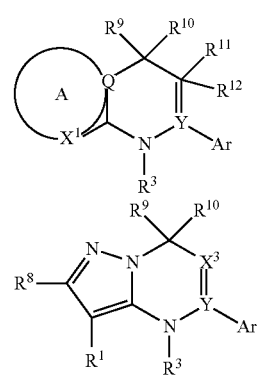

[Formula 1]

Patent Literature 2 discloses compounds or salts thereof represented by the formula below. This literature also describes that these compounds or salts thereof have a calcium-sensing receptor (CaSR) control action (agonist activity or antagonist activity) and secretion control actions of parathyroid hormone (PTH) thereby.

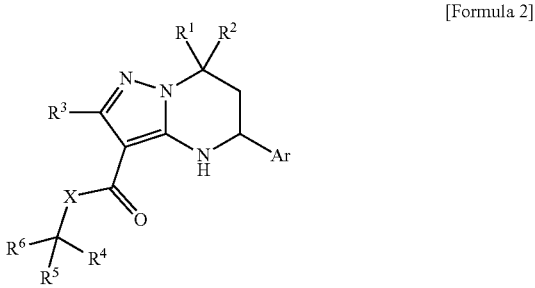

[Formula 2]

For heart failure, Non Patent Literatures 1 and 2 describe that parathyroid hormone treatment improves cardiac function, while Non Patent Literature 3 describes that parathyroid hormone treatment deteriorates cardiac function. Thus, the relationship of parathyroid hormone treatment and cardiac function improvement has not yet been fully elucidated.

Non Patent Literature 4 describes that CaSR inhibitor Calhex231 improves cardiac hypertrophy in aortic banding (TAC) models, but the effect after cardiac hypofunction is not elucidated. Non Patent Literature 5 describes the result of Calhex231 dosing and shows that the Calhex231 dosing after cardiac loading fails to improve cardiac hypofunction. Furthermore, Non Patent Literature 6 describes that CaSR antagonists nullify cardioprotective effects in ischemic pre-conditioning models. So, the relationship of CaSR inhibition and the improvement of cardiac hypofunction or survival rate has not yet been fully elucidated.

For pulmonary hypertension, it has recently been reported that, in pulmonary arterial smooth muscle cells (PASMCs) isolated from pulmonary hypertension patients, CaSR is overexpressed, and the hyperactivity thereby causes, for example, abnormal proliferation of pulmonary vascular tissues. Furthermore, it has been reported that Compound NPS-2143, which has CaSR antagonistic activity, suppressed cardiac hypertrophy, elevated right ventricular systolic pressure, fibrosis of cardiac muscle tissue, pulmonary vascular remodeling or the like in monocrotaline (MCT)-induced pulmonary hypertension rats and hypoxia-induced pulmonary hypertension (HPH) mice (Non Patent Literatures 7 to 11). However, the medical need for therapeutic agents for pulmonary hypertension is still high, and development of the medicament for preventing or treating pulmonary hypertension, having excellent properties in terms of efficacy, specificity, and low toxicity, has been desired.

CITATION LIST

Patent Literature

Patent Literature 1:
WO2004/017908
Patent Literature 2:
JP 2005-239611 A

Non Patent Literature

Non Patent Literature 1:
Cardiovascular research, 77: 722-731, 2008
Non Patent Literature 2:
Cardiovascular research, 93: 330-339, 2012
Non Patent Literature 3:
Experimental and molecular medicine 42, 61-68, 2010
Non Patent Literature 4:
Cell Physiol. Biochem., 36: 1597-1612, 2015
Non Patent Literature 5:
Cell Physiol. Biochem., 33: 557-568, 2014
Non Patent Literature 6:
Am. J. Physiol. Heart Circ. Physiol., 299: H1309-H1317, 2010
Non Patent Literature 7:
Circ. Res., 111(4): 469-481, 2012
Non Patent Literature 8:
Circ. Res., 112(4): 640-650, 2013
Non Patent Literature 9:
YAKUGAKU ZASSHI, 133(12):1351-1359, 2013
Non Patent Literature 10:
J. Smooth Muscle Res., 50: 8-17, 2014
Non Patent Literature 11:
Hypertens Res. 37(2): 116-124, 2014

SUMMARY OF INVENTION

Technical Problem

An object of the present invention is to provide a compound or a salt thereof having a calcium-sensing receptor antagonistic activity, and being expected to be useful as an agent for preventing or treating heart failure, pulmonary hypertension, or the like.

Solution to Problem

The present inventors have found that the compound represented by the formula (1) below or a salt thereof has a calcium-sensing receptor antagonistic activity, and is expected to be useful as an agent for preventing or treating heart failure, pulmonary hypertension, or the like. Based on the findings, the present inventors had intensive studies, and consequently have completed the present invention.

That is, the present invention is as follows.

[1] A compound represented by formula (I):

[Formula 3]

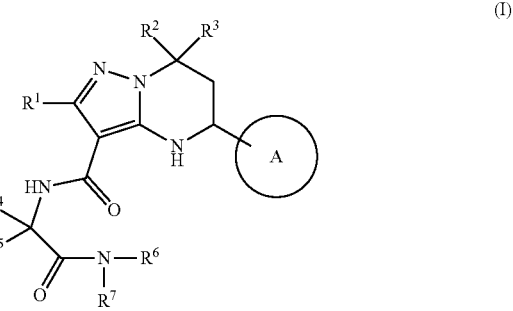

wherein

Ring A represents an optionally further substituted aromatic ring;

$R^1$ represents a hydrogen atom, an optionally substituted alkyl group, an optionally substituted alkylthio group, or an optionally substituted alkoxy group;

$R^2$ and $R^3$ each independently represent an optionally substituted alkyl group, or $R^2$ and $R^3$ may form an optionally further substituted ring together with an adjacent carbon atom;

$R^4$ and $R^5$ each independently represent an optionally substituted aromatic ring group or optionally substituted alkyl group;

$R^6$ and $R^7$ each independently represent a hydrogen atom or an optionally substituted alkyl group, or a salt thereof (hereinafter, also referred to as "compound (I)").

[2] The compound or a salt thereof according to [1], wherein Ring A is a benzene ring.

[3] The compound or a salt thereof according to [1], wherein $R^1$ is a hydrogen atom or a $C_{1-6}$ alkyl group.

[4] The compound or a salt thereof according to [1], wherein each of $R^2$ and $R^3$ is $C_{1-6}$ alkyl.

[5] The compound or a salt thereof according to [1], wherein $R^4$ is a $C_{6-14}$ aryl group which is optionally substituted with one to five $C_{1-6}$ alkyl groups.

[6] The compound or a salt thereof according to [1], wherein $R^5$ is a $C_{1-6}$ alkyl group.

[7] The compound or a salt thereof according to [1], wherein $R^6$ is a hydrogen atom or a $C_{1-6}$ alkyl group.

[8] The compound or a salt thereof according to [1], wherein $R^7$ is a hydrogen atom or a $C_{1-6}$ alkyl group which is optionally substituted with one to three substituents selected from the group consisting of (a) a carbamoyl group,
(b) a carboxy group,
(c) a hydroxy group, and
(d) a phenyl group.

[9] The compound or a salt thereof according to [1], wherein

Ring A is a benzene ring;
$R^1$ is a hydrogen atom or a $C_{1-6}$ alkyl group;
each of $R^2$ and $R^3$ is a $C_{1-6}$ alkyl group;

$R^4$ is a $C_{6-14}$ aryl group which is optionally substituted with one to five $C_{1-6}$ alkyl groups;

$R^5$ is a $C_{1-6}$ alkyl group;

$R^6$ is a hydrogen atom or a $C_{1-6}$ alkyl group; and $R^7$ is a hydrogen atom or a $C_{1-6}$ alkyl group which is optionally substituted with one to three substituents selected from the group consisting of (a) a carbamoyl group, (b) a carboxy group, (c) a hydroxy group, and (d) a phenyl group.

[10] (5R)—N-((2R)-1-(((2S)-1-Amino-1-oxopropan-2-yl)amino)-2-(4-ethylphenyl)-1-oxobutan-2-yl)-2,7,7-trimethyl-5-phenyl-4,5,6,7-tetrahydropyrazolo[1,5-a]pyrimidine-3-carboxamide or a salt thereof.

[11] (5R)—N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide or a salt thereof.

[12] (5R)—N-(1-(((2S)-1-Amino-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide or a salt thereof.

[13] (5R)—N-(1-(((2S)-1-Amino-3-methyl-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide or a salt thereof.

[14] A medicament comprising the compound or a salt thereof according to [1].

[15] The medicament according to [14], wherein the medicament is a calcium-sensing receptor antagonist.

[16] The medicament according to [14], wherein the medicament is an agent for preventing or treating heart failure.

[17] The medicament according to [14], wherein the medicament is an agent for preventing or treating pulmonary hypertension.

[18] The compound or a salt thereof according to [1], for use in preventing or treating heart failure.

[19] The compound or a salt thereof according to [1], for use in preventing or treating pulmonary hypertension.

[20] A method of antagonizing a calcium-sensing receptor in a mammal, comprising administering an effective amount of the compound or a salt thereof according to [1] to the mammal.

[21] A method of preventing or treating heart failure in a mammal, comprising administering an effective amount of the compound or a salt thereof according to [1] to the mammal.

[22] A method of preventing or treating pulmonary hypertension in a mammal, comprising administering an effective amount of the compound or a salt thereof according to [1] to the mammal.

[23] Use of the compound or a salt thereof according to [1], for production of an agent for preventing or treating heart failure.

[24] Use of the compound or a salt thereof according to [1], for production of an agent for preventing or treating pulmonary hypertension.

Advantageous Effects of Invention

According to the present invention, a compound having a calcium-sensing receptor antagonistic activity and being expected to be useful as an agent for preventing or treating heart failure, pulmonary hypertension, or the like is provided.

DETAILED DESCRIPTION OF THE INVENTION

Figure 1:
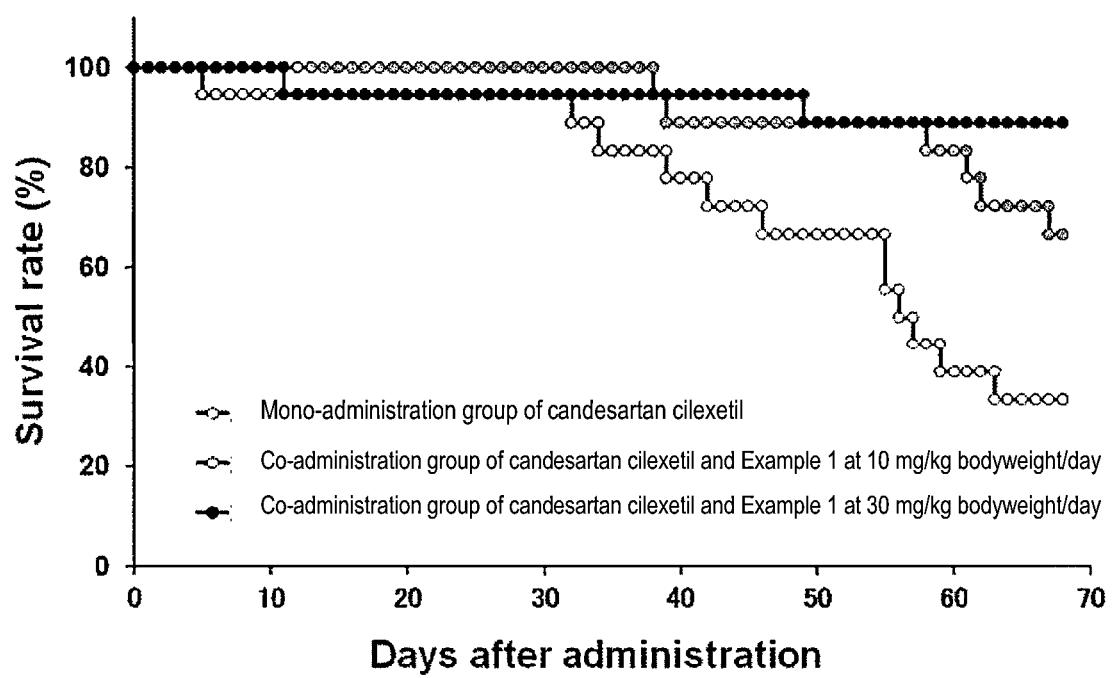
FIG. 1 is a graph showing a result of Test Example 5 "Effect of Compound of Example 1 on Survival Rate of Heart Failure Animal Model", that is, survival rates of each of the mono-administration group of candesartan cilexetil, the co-administration group of candesartan cilexetil and the compound of Example 1 at 10 mg/kg bodyweight/day, and the co-administration group of candesartan cilexetil and the compound of Example 1 at 30 mg/kg bodyweight/day (log-rank test, the co-administration group of candesartan cilexetil and the compound of Example 1 at 10 mg/kg bodyweight/day ($p<0.05$), the co-administration group of candesartan cilexetil and the compound of Example 1 at 30 mg/kg bodyweight/day ($p<0.01$)).

Hereinafter, the present invention will be described in detail.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ is aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_1$_alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_6$-14 aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterodyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),

(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_1$ alkylsulfonyloxy group (e.g., methylsulfonyloxy, trifluoromethylsulfonyloxy),
(19) a $C_{6-14}$ aryl-sulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, etzylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{1-6}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazoLyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, p-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazeoanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisotgiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenotniazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-R-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbDnyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocaroamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-11}$ aryl-thiocarbamoyl group (e.g., phenylthiocarbanoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{1-6}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-15}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarocnyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1}$_alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyL group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

$_3H_7)$—, —CH(CH(CH$_3$)$_2$)—, —(CH(CH$_3$))$_2$—, —CH$_2$—CH(CH$_3$)—, —CH(CH$_3$)—CH$_2$—, —CH—CH$_2$—C(CH$_3$)$_2$—, —C(CH$_3$)$_2$—CH$_2$—CH$_2$—, —CH$_2$—CH$_2$—CH$_2$—C(CH$_3$)$_2$— and —C(CH$_3$)$_2$—CH$_2$—CH$_2$—CH$_2$—.

In the present specification, examples of the "$C_{2-6}$ alkenylene group" include —CH=CH—, —CH$_2$—CH=CH—, —CH=CH—CH$_2$—, —C(CH$_3$)$_2$—CH=CH—, —CH=CH—C(CH$_3$)$_2$—, —CH$_2$—CH=CH—CH$_2$—, —CH=CH—CH$_2$—CH$_2$—, —CH$_2$—CH$_2$—CH=CH—, —CH=CH—CH$_2$—CH$_2$—CH$_2$— and —CH$_2$—CH$_2$—CH$_2$—CH=CH—.

In the present specification, examples of the "$C_{2-6}$ alkynylene group" include —C≡C—, —CH$_2$—C≡C—, —C≡C—CH$_2$—, —C(CH$_3$)$_2$—C≡C—, —C≡C—C(CH$_3$)$_2$—, —CH$_2$—C≡C—CH$_2$—, —CH$_2$—CH$_2$—C≡C—, —C≡C—CH$_2$—CH$_2$—, —C≡C—C≡C—, —C≡C≡CH$_2$—CH$_2$— and —CH$_2$—CH$_2$—CH$_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetra ole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridne, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphtayridine, tetrahydroquinazoline, tetrahydrocinnoline, tetrahydrocarbazole, tetrahydro-p-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

As used herein, examples of the "aromatic ring" includes "$C_{6-14}$ aromatic hydrocarbon ring" and "aromatic heterocycle".

As used herein, examples of the "aromatic ring group" include "$C_{6-14}$ aryl group" and "aromatic heterocyclic group".

As used herein, examples of the "ring" includes, "hydrocarbon ring" (e.g., $C_{6-14}$ aromatic hydrocarbon ring, $C_{3-10}$ cycloalkane, $C_{3-10}$ cycloalkene) and "heterocycle" (e.g., aromatic heterocycle, non-aromatic heterocycle).

Hereinafter, the definition of each symbol in compound (I) will be described in detail.

Ring A represents an aromatic ring which is optionally further substituted.

In an embodiment, the "aromatic ring" in the "optionally further substituted aromatic ring" of Ring A is a $C_{6-14}$ aromatic hydrocarbon ring (preferably a benzene ring), and the "aromatic ring" in the "optionally further substituted aromatic ring" of Ring A may have 1 to 5 substituents at substitutable positions. Examples of the substituent include a substituent selected from the [Substituent Group A]. When there are a plurality of substituents, each of the substituents may be the same or different each other.

Ring A is preferably an optionally further substituted benzene ring, and more preferably a benzene ring.

$R^1$ represents a hydrogen atom, an optionally substituted alkyl group, an optionally substituted alkylthio group, or an optionally substituted alkoxy group.

Examples of the "alkyl group" in the "optionally substituted alkyl group" of $R^1$ include a "$C_{1-6}$ alkyl group".

Examples of the "alkylthio group" in the "optionally substituted alkylthio group" of $R^1$ include a "$C_{1-6}$ alkylthio group".

Examples of the "alkoxy group" in the "optionally substituted alkoxy group" of $R^1$ include a "$C_{1-6}$ alkoxy group".

The "alkyl group" in the "optionally substituted alkyl group", the "alkylthio group" in the "optionally substituted alkylthio group", and the "alkoxy group" in the "optionally substituted alkoxy group" of $R^1$ each are optionally have one to three substituents at substitutable positions. Examples of such substituents include a substituent selected from the [substituent group A]. When there are two or more substituents, each of the substituents may be the same or different each other.

$R^1$ is preferably a hydrogen atom, or an optionally substituted $C_{1-6}$ alkyl group (e.g., methyl), more preferably a hydrogen atom or a $C_{1-6}$ alkyl group (e.g., methyl).

$R^2$ and $R^3$ each independently represent an optionally substituted alkyl group, or $R^2$ and $R^3$ form an optionally further substituted ring together with an adjacent carbon atom.

Examples of the "alkyl group" in the "optionally substituted alkyl group" of $R^2$ and $R^3$ include a "$C_{1-6}$ alkyl group". The "alkyl group" in the "optionally substituted alkyl group" optionally has one to three substituents at substitutable positions. Examples of such substituents include a substituent selected from the [substituent group A]. When there are two or more substituents, each of the substituents may be the same or different each other.

The "ring" in the "optionally further substituted ring" formed by $R^2$ and $R^3$ with an adjacent carbon atom includes a "$C_{3-14}$~ cycloalkane". The "ring" in the "optionally further substituted ring" optionally have one to three substituents at substitutable positions. Examples of such substituents include a substituent selected from the [substituent group A]. When there are two or more substituents, each of the substituents may be the same or different each other.

$R^2$ is preferably a hydrogen atom or optionally substituted $C_{1-6}$ alkyl group (e.g., methyl), more preferably a hydrogen atom or a $C_{1-6}$ alkyl group (e.g., methyl), and furthermore preferably a $C_{1-6}$ alkyl group (e.g., methyl).

$R^3$ is preferably a hydrogen atom or an optionally substituted $C_{1-6}$ alkyl group (e.g., methyl), more preferably a hydrogen atom or a $C_{1-6}$ alkyl group (e.g., methyl), and furthermore preferably a $C_{1-6}$ alkyl group (e.g., methyl).

$R^4$ and $R^5$ each independently represent an optionally substituted aromatic ring group or an optionally substituted alkyl group.

Examples of the "aromatic ring group" in the "optionally substituted aromatic ring group" of $R^4$ and $R^5$ includes a "$C_{6-14}$ aryl group" or an "aromatic heterocyclic group". The "aromatic ring group" in the "optionally substituted aromatic ring group" optionally has one to three substituents at substitutable positions. Examples of such substituents include a substituent selected from the [substituent group A]. When there are two or more substituents, each of the substituents may be the same or different each other.

Example of the "alkyl group" in the "optionally substituted alkyl group" of $R^4$ and $R^5$ includes a "$C_{1-6}$ alkyl group". The "alkyl group" in the "optionally substituted alkyl group" optionally has one to three substituents at substitutable positions. Examples of such substituents include a substituent selected from the [substituent group A]. When there are two or more substituents, each of the substituents may be the same or different each other.

$R^4$ is preferably an optionally substituted $C_{6-14}$ aryl group (e.g., phenyl), more preferably a $C_{6-14}$ aryl group (e.g., phenyl) which is optionally substituted with one to five $C_{1-6}$ alkyl groups (e.g., ethyl), and furthermore preferably a phenyl group substituted with an ethyl group (e.g., a 4-ethylphenyl group).

$R^5$ is preferably an optionally substituted $C_{1-6}$ alkyl group (e.g., methyl, ethyl), more preferably a $C_{1-6}$ alkyl group (e.g., methyl, ethyl).

$R^6$ and R, each independently represent a hydrogen atom or an optionally substituted alkyl group.

The "alkyl group" in the "optionally substituted alkyl group" of $R^6$ and $R^7$ includes a "$C_{1-6}$ alkyl group". The "alkyl group" in the "optionally substituted alkyl group" may have one to three substituents at substitutable positions. Examples of such substituents include a substituent selected from the [substituent group A]. When there are two or more substituents, each of the substituents may be the same or different each other.

$R^6$ is preferably a hydrogen atom or an optionally substituted $C_{1-6}$ alkyl group (e.g., methyl), more preferably a hydrogen atom or a $C_{1-6}$ alkyl group (e.g., methyl).

$R^7$ is preferably a hydrogen atom or an optionally substituted $C_{1-6}$ alkyl group (e.g., methyl, ethyl, propyl, butyl, pentyl).

$R^7$ is more preferably a hydrogen atom or a $C_{1-6}$ alkyl group (e.g., methyl, ethyl, propyl, butyl, pentyl) which is optionally substituted with one to three substituents selected from the group consisting of
   (a) a carbamoyl group,
   (b) a carboxy g coup,
   (c) a $C_{1-6}$ alkyl group (e.g., methyl),
   (d) an amino group,
   (e) a hydroxy group, and
   (f) a phenyl group, and more specifically, $R^7$ is a hydrogen atom or a $C_{1-6}$ alkyl group (e.g., methyl, ethyl, propyl, butyl, pentyl) which is optionally substituted with one to three substituents selected from the group consisting of
   (a) a carbamoyl group,
   (b) a carboxy group,
   (c) a hydroxy group, and
   (d) a phenyl group.

$R^7$ is furthermore preferably a $C_{1-6}$ alkyl group (e.g., methyl, ethyl, propyl, butyl, pentyl) which is substituted with at least one carbamoyl group and optionally further substituted with one or two substituents selected from the group consisting of
(a) a carbamoyl group,
(b) a carboxy group,
(c) a $C_{1-6}$ alkyl group (e.g., methyl),
(d) an amino group,
(e) a hydroxy group, and
(f) a phenyl group.

$R^7$ is even more preferably a $C_{1-6}$ alkyl group (e.g., methyl, ethyl, propyl) which is optionally substituted with a carbamoyl group.

$R^7$ is still more preferably a $C_{1-6}$ alkyl group (e.g., ethyl, propyl) which is substituted with a carbamoyl group.

When $R^7$ is a $C_{1-6}$ alkyl group substituted with a carbamoyl group, it should be preferred that the carbamoyl group be attached to the alpha carbon that is the carbon atom closest to the nitrogen atom to which the $C_{1-6}$ alkyl group as $R^7$ is attached.

Examples of the preferred aspect of compound (I) include the following compounds.

[Compound A]
The compound (I), wherein
Ring A is an optionally further substituted benzene ring;
$R^1$ is a hydrogen atom or an optionally substituted $C_{1-6}$ alkyl group (e.g., methyl);
$R^2$ is a hydrogen atom or an optionally substituted $C_{1-6}$ alkyl group (e.g., methyl);
$R^3$ is a hydrogen atom or an optionally substituted $C_{1-6}$ alkyl group (e.g., methyl);
$R^4$ is an optionally substituted $C_{6-14}$ aryl group (e.g., phenyl);
$R^5$ is an optionally substituted $C_{1-6}$ alkyl group (e.g., methyl, ethyl);
$R^6$ is a hydrogen atom or an optionally substituted $C_{1-6}$ alkyl group (e.g., methyl); and
$R^7$ is a hydrogen atom or an optionally substituted $C_{1-6}$ alkyl group (e.g., methyl, ethyl, propyl, butyl, pentyl).

[Compound B]
The compound (I), wherein
Ring A is a benzene ring;
$R^1$ is a hydrogen atom or a $C_{1-6}$ alkyl group (e.g., methyl);
$R^2$ is a hydrogen atom or a $C_{1-6}$ alkyl group (e.g., methyl);
$R^3$ is a hydrogen atom or a $C_{1-6}$ alkyl group (e.g., methyl);
$R^4$ is a $C_{6-14}$ aryl group (e.g., phenyl) which is optionally substituted with one to five $C_{1-6}$ alkyl groups (e.g., ethyl);
$R^5$ is a $C_{1-6}$ alkyl group (e.g., methyl, ethyl);
$R^6$ is a hydrogen atom or a $C_{1-6}$ alkyl group (e.g., methyl); and
$R^7$ is a hydrogen atom or a $C_{1-6}$ alkyl group (e.g., methyl, ethyl, propyl, butyl, pentyl) which is optionally substituted with one to three substituents selected from the group consisting of
(a) a carbamoyl group,
(b) a carboxy group,
(c) a $C_{1-6}$ alkyl group (e.g., methyl);
(d) an amino group,
(e) a hydroxy group, and
(f) a phenyl group.

[Compound B']
The compound (I), wherein
Ring A is a benzene ring;
$R^1$ is a hydrogen atom or a $C_{1-6}$ alkyl group (e.g., methyl);
$R^2$ is a hydrogen atom or a $C_{1-6}$ alkyl group (e.g., methyl);
$R^3$ is a hydrogen atom or a $C_{1-6}$ alkyl group (e.g., methyl);
$R^4$ is a $C_{6-14}$ aryl group (e.g., phenyl) which is optionally substituted with one to five $C_{1-6}$ alkyl groups (e.g., ethyl);
$R^5$ is a $C_{1-6}$ alkyl group (e.g., methyl, ethyl);
$R^6$ is a hydrogen atom or a $C_{1-6}$ alkyl group (e.g., methyl); and
$R^7$ is a hydrogen atom or a $C_{1-6}$ alkyl group (e.g., methyl, ethyl, propyl, butyl, pentyl) which is optionally substituted with one to three substituents selected from the group consisting of
(a) a carbamoyl group,
(b) a carboxy group,
(c) a hydroxy group, and
(d) a phenyl group.

[Compound C]
The compound (I), wherein
Ring A is a benzene ring;
$R^1$ is a hydrogen atom or a $C_{1-6}$ alkyl group (e.g., methyl);
$R^2$ is a hydrogen atom or a $C_{1-6}$ alkyl group (e.g., methyl);
$R^3$ is a hydrogen atom or a $C_{1-6}$ alkyl group (e.g., methyl);
$R^4$ is a phenyl group substituted with an ethyl group (e.g., a 4-ethylphenyl group);
$R^5$ is a $C_{1-6}$ alkyl group (e.g., methyl, ethyl);
$R^6$ is a hydrogen atom or a $C_{1-6}$ alkyl group (e.g., methyl); and
$R^7$ is a $C_{1-6}$ alkyl group (e.g., methyl, ethyl, propyl, butyl, pentyl) which is substituted with at least one carbamoyl group and optionally further substituted with one or two substituents selected from the group consisting of
(a) a carbamoyl group,
(b) a carboxy group,
(c) a $C_{1-6}$ alkyl group (e.g., methyl),
(d) an amino group,
(e) a hydroxy group, and
(f) a phenyl group.

[Compound C']
The compound (I), wherein
Ring A is a benzene ring;
$R^1$ is a hydrogen atom or a $C_{1-6}$ alkyl group (e.g., methyl);
$R^2$ is a hydrogen atom or a $C_{1-6}$ alkyl group (e.g., methyl);
$R^3$ is a hydrogen atom or a $C_{1-6}$ alkyl group (e.g., methyl);
$R^4$ is a phenyl group substituted with an ethyl group (e.g., a 4-ethylphenyl group);
$R^5$ is a $C_{1-6}$ alkyl group (e.g., methyl, ethyl);
$R^6$ is a hydrogen atom or a $C_{1-6}$ alkyl group (e.g., methyl); and
$R^7$ is a $C_{1-6}$ alkyl group (e.g., methyl, ethyl, propyl, butyl, pentyl) which is substituted with at least one carbamoyl group and optionally further substituted with one or two substituents selected from the group consisting of
(a) a carbamoyl group,
(b) a carboxy group,
(c) a hydroxy group, and
(d) a phenyl group.

[Compound D]
The compound (I), wherein
Ring A is a benzene ring;
$R^1$ is a hydrogen atom or a $C_{1-6}$ alkyl group (e.g., methyl);
$R^2$ is a hydrogen atom or a $C_{1-6}$ alkyl group (e.g., methyl);
$R^3$ is a hydrogen atom or a $C_{1-6}$ alkyl group (e.g., methyl);
$R^4$ is a phenyl group substituted with an ethyl group (e.g., a 4-ethylphenyl group);
$R^5$ is a $C_{1-6}$ alkyl group (e.g., methyl, ethyl);

$R^6$ is a hydrogen atom or a $C_{1-6}$ alkyl group (e.g., methyl); and $R^7$ is a $C_16$ alkyl group (e.g., methyl, ethyl, propyl) which is optionally substituted with a carbamoyl group.

[Compound E]

The compound (I), wherein

Ring A is a benzene ring;

$R^1$ is a hydrogen atom or a $C_{1-6}$ alkyl group (e.g., methyl);

$R^2$ is a hydrogen atom or a $C_{1-6}$ alkyl group (e.g., methyl);

$R^3$ is a hydrogen atom or a $C_{1-6}$ alkyl group (e.g., methyl);

$R^4$ is a phenyl group substituted with an ethyl group (e.g., a 4-ethylphenyl group);

$R^5$ is a $C_{1-6}$ alkyl group (e.g., methyl, ethyl);

$R^6$ is a hydrogen atom or a $C_{1-6}$ alkyl group (e.g., methyl); and $R^7$ is a $C_{1-6}$ alkyl group (e.g., ethyl, propyl) which is substituted with a carbamoyl group.

Specific examples of compound (I) include compounds of Examples 1 to 33 described below.

Preferred examples of compound (I) specifically include:

(5R)—N-((2R)-1-(((2S)-1-amino-1-oxopropan-2-yl)amino)-2-(4-ethylphenyl)-1-oxobutan-2-yl)-2,7,7-trimethyl-5-phenyl-4,5,6,7-tetrahydropyrazolo[1,5-a]pyrimidine-3-carboxamide or a salt thereof;

(5R)—N-(1-(((2S)-1-amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide or a salt thereof;

(5R)—N-(1-(((2S)-1-amino-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide or a salt thereof; and (5R)—N-(1-(((2S)-1-amino-3-methyl-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide or a salt thereof.

When compound (I) is a salt, examples of the salt include a salt with an inorganic base, an ammonium salt, a salt with an organic base, a salt with an inorganic acid, a salt with an organic acid, and a salt with a basic or acidic amino acid.

Preferable examples of the salt with an inorganic base include an alkali metal salt such as a sodium salt or a potassium salt; an alkaline earth metal salt such as a calcium salt, a magnesium salt, or a barium salt; and an aluminum salt.

Preferable examples of the salt with an organic base include salts with trimethylamine, triethylamine, pyridine, picoline, ethanolamine, diethanolamine, triethanolamine, dicyclohexylamine, and N,N'-dibenzylethylenediamine.

Preferable examples of the salt with an inorganic acid include salts with hydrochloric acid, hydrobromic acid, nitric acid, sulfuric acid and phosphoric acid.

Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

Preferable examples of the salt with a basic amino acid include salts with arginine, lysine, and ornithine.

Preferable examples of the salt with an acidic amino acid include salts with aspartic acid and glutamic acid.

Among these salts, pharmaceutically acceptable salts will be preferred.

Hereinafter, methods for producing compound (I) are described.

The raw materials and reagents used in each step of the following production methods, as well as the resulting compounds, each may form a salt. Examples of the salt include those similar to the salts of compound (I) mentioned above.

When the compound obtained in each step is a free compound, the compound can be converted to a salt of interest by a method known per se. On the other hand, when the compound obtained in each step is a salt, the compound can be converted into a free form or another type of salt of interest by a method known per se.

The compound obtained in each step can be used in the next reaction as remained in a reaction solution or after being obtained as a crude product. Alternatively, the compound obtained in each step may be isolated and/or purified from the reaction mixture by separation means such as concentration, crystallization, recrystallization, distillation, solvent extraction, fractionation, or chromatography according to a conventional method.

When raw materials or reagent compounds for each step are commercially available, the commercial products can be used as it is.

In the reaction of each step, the reaction time may vary depending on the reagent and solvent to be used, but unless otherwise specified, it is generally 1 minute to 48 hours, preferably 10 minutes to 16 hours.

In the reaction of each step, the reaction temperature may vary depending on the reagent and solvent to be used, but unless otherwise specified, it is generally −78° C. to 300° C., preferably −78° C. to 150° C.

In the reaction of each step, the pressure may vary depending on the reagent and solvent to be used, but unless otherwise specified, it is generally 1 atm to 20 atm, preferably 1 atm to 3 atm.

In the reaction of each step, a microwave synthesizer such as Initiator, manufactured by Biotage Co., may be used. The reaction temperature may vary depending on the reagent and solvent to be used, but unless otherwise specified, it is generally room temperature to 300° C., preferably 50° C. to 250° C. The reaction time may vary depending on the reagent and solvent to be used, but unless otherwise specified, it is generally 1 minute to 48 hours, preferably 1 minute to 8 hours.

In the reaction of each step, the reagent is used, unless otherwise specified, in an amount of 0.5 to 20 equivalents, preferably 0.8 to 5 equivalents, relative to the substrate. When the reagent is used as a catalyst, the reagent is used in an amount of 0.001 to 1 equivalent, preferably 0.01 to 0.2 equivalents, relative to the substrate. When the reagent also serves as a reaction solvent, the reagent is used in an amount of the solvent.

In the reactions of each step, unless otherwise specified, the reactions are carried out by solvent-free, or carried out in an appropriate solvent in the form as a solution or suspension. Specific examples of the solvent include the solvent described in Examples or the following solvents:

Alcohols: methanol, ethanol, tert-butyl alcohol, 2-methoxyethanol, and the like;

Ethers: diethyl ether, diphenyl ether, tetrahydrofuran, 1,2-dimethoxyethane, and the like;

Aromatic hydrocarbons: chlorobenzene, toluene, xylene, and the like;

Saturated hydrocarbons: cyclohexane, hexane, and the like;

Amides: N,N-dimethylformamide, N-methylpyrrolidone, and the like;

Halogenated hydrocarbons: dichloromethane, carbon tetrachloride, and the like;

Nitriles: acetonitrile, and the like;

Sulfoxides: dimethyl sulfoxide, and the like;
Aromatic organic bases: pyridine, and the like;
Acid anhydrides: acetic anhydride, and the like;
Organic acids: formic acid, acetic acid, trifluoroacetic acid, and the like;
Inorganic acids: hydrochloric acid, sulfuric acid, and the like;
Esters: ethyl acetate, and the like;
Ketones: acetone, methyl ethyl ketone, and the like; and
Water.

The above solvents may be used in a combination of two or more at an appropriate ratio.

When using a base in the reaction of each step, examples of the base that can be used include the base described in Examples or the following bases.
Inorganic bases: sodium hydroxide, magnesium hydroxide, and the like;
Basic salts: sodium carbonate, calcium carbonate, sodium bicarbonate, and the like;
Organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, and the like;
Metal alkoxides: sodium ethoxide, potassium tert-butoxide, and the like;
Alkali metal hydrides: sodium hydride, and the like;
Metal amides: sodium amide, lithium diisopropylamide, lithium hexamethyldisilazide, and the like; and
Organolithiums: n-butyl lithium, and the like.

When using an acid or an acidic catalyst in the reaction of each step, examples of the acids or acidic catalyst that can be used include the acid or acidic catalysts described in Examples, or the following acids or acidic catalysts:
Inorganic acids: hydrochloric acid, sulfuric acid, nitric acid, hydrobromic acid, phosphoric acid, and the like;
Organic acids: acetic acid, trifluoroacetic acid, citric acid, p-toluenesulfonic acid, 10-camphorsulfonic acid, and the like; and
Lewis acids: boron trifluoride diethyl ether complex, zinc iodide, anhydrous aluminum chloride, anhydrous zinc chloride, anhydrous ferric chloride, and the like.

The reaction of each step, unless otherwise specified, is carried out according to a method known per se, for example, a method described in "Jikken Kagaku Kouza (Series of experimental chemistry), 5th Edition", Volume 13 to Volume 19 (edited by The Chemical Society of Japan); "Shin Jikken Kagaku Kouza (New series of experimental chemistry)", Volume 14 to Volume 15 (edited by The Chemical Society of Japan); "Seimitsu Yuki Kagaku (Fine Organic Chemistry), Revised 2nd Edition" (L. F. Tietze, Th. Eicher, Nankodo Co., Ltd.); "Organic named reactions: the reaction mechanism and essence", Revised version (written by Togo Hideo, KODANSHA LTD.); "ORGANIC SYNTHESES", Collective Volume I-VII (John Wiley & Sons Inc.; Modern Organic Synthesis in the Laboratory A Collection of Standard Experimental Procedures (written by Jie Jack Li, published by OXFORD UNIVERSITY); "Comprehensive Heterocyclic Chemistry III", Vol. 1 to Vol. 14 (Elsevier Japan Co., Ltd.); "Strategic applications of named reactions in organic synthesis" (translation supervised by Tomioka Kiyoshi, published by Kagaku-Dojin Publishing Co., Inc); "Comprehensive Organic Transformations" (VCH Publishers Inc.) published in 1989; or the like, or a method described in the Examples.

In each step, a protection or deprotection reaction of a functional group is carried out according to a method known per se, for example, a method described in "Protective Groups in Organic Synthesis, 4th Ed." (written by Theodora W. Greene, Peter G. M. Wuts), published by Wiley-Interscience, 2007; "Protecting Groups 3rd Ed." (written by P. J. Kocienski) published by Thieme Corporation, 2004; or the like, or a method described in the Examples.

Examples of the protecting group for a hydroxyl group such as in alcohol or a phenolic hydroxyl group include an ether type protecting group such as methoxymethyl ether, benzyl ether, t-butyl dimethyl silyl ether, or tetrahydropyranyl ether; a carboxylic acid ester-type protecting group such as acetate; a sulfonic acid ester type protecting group such as methanesulfonic acid ester; and a carbonate type protecting group such as t-butyl carbonate.

Examples of the protecting group for a carbonyl group in aldehyde include an acetal-type protecting group such as dimethyl acetal; and a cyclic acetal type protecting group such as cyclic 1,3-dioxane.

Examples of the protecting group for a carbonyl group in ketone include a ketal type protecting group such as dimethyl ketal; a cyclic ketal type protecting group such as cyclic 1,3-dioxane; an oxime protecting group such as O-methyloxime; and a hydrazone type protecting group such as N,N-dimethyl hydrazone.

Examples of the protecting group for a carboxyl group include an ester type protecting group such as methyl ester; and an amide-type protecting group such as N,N-dimethyl amide.

Examples of the protecting group for thiol include an ether type protecting group such as benzyl thioether; and an ester-type protecting group such as thioacetate, thiocarbonate, thiocarbamate.

Examples of the protecting group for an amino group or an aromatic hetero ring such as imidazole, pyrrole and indole include a carbamate type protecting group such as benzyl carbamate; an amide type protecting group such as acetamide; an alkyl amine type protecting group such as N-triphenylmethyl amine; and a sulfonamide type protecting group such as methane sulfonamide.

Removal of the protecting group is carried out according to a method known per se, for example, a method using an acid, a base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and a reducing method.

In each step, when a reduction reaction is performed, examples of the reducing agent used include metal hydrides such as lithium aluminum hydride, sodium triacetoxyborohydride, sodium cyanoborohydride, diisobutylaluminum hydride (DIBAL-H), sodium borohydride, triacetoxy borohydride tetramethylammonium; boranes such as borane tetrahydrofuran complex; Raney nickel; Raney cobalt; hydrogen; and formic acid. When reducing the carbon-carbon double bond or triple bond, a method using a catalyst such as a palladium-carbon or Lindlar catalyst may be used.

In each step, when an oxidation reaction is performed, examples of the oxidizing agents to be used include peracids such as m-chloro peroxybenzoic acid (MCPBA), hydrogen peroxide, t-butyl hydroperoxide; perchlorates such as tetrabutylammonium perchlorate; chlorates such as sodium chlorate; chlorites such as sodium chlorite; periodic acids such as sodium periodate; high valent iodine reagents such as iodosyl benzene; reagents having manganese such as manganese dioxide, potassium permanganate; leads such as lead tetraacetate; reagents having chromium such as pyridinium chlorochromate (PCC), pyridinium dichromate (PDC), Jones reagents; halogen compounds such as N-bromosuccinimide (NBS); oxygen; ozone; sulfur trioxide-pyridine complex; osmium tetraoxide; zelen dioxide; and 2,3-dichloro-5,6-dicyano-1,4-benzoquinone (DDQ).

In each step, when a radical cyclization reaction is performed, examples of the radical initiators to be used include azo compounds such as azobis isobutyronitrile (AIBN); water-soluble radical initiators such as 4-4'-azobis-4-cyanopentanoic acid (ACPA); triethylboron in the presence of air or oxygen; and benzoyl peroxide. Furthermore, examples of the radical reaction reagent to be used include tributylstannane, tris trimethylsilyl silane, 1,1,2,2-tetraphenyl disilane, diphenylsilane, and samarium iodide.

In each step, when Wittig reaction is performed, examples of the Wittig reagent to be used include alkylidene phosphoranes. The alkylidene phosphoranes can be prepared by a method known per se, for example, a method by reacting a phosphonium salt with a strong base.

In each step, when Horner-Emmons reaction is performed, examples of the reagent to be used include phosphonoacetic acid esters such as methyl dimethylphosphonoacetate, ethyl diethylphosphonoacetate; and bases such as alkali metal hydrides, organolithiums.

In each step, when Friedel-Crafts reaction is performed, examples of the reagents to be used include Lewis acids and acid chlorides or alkylating agents (e.g., alkyl halides, alcohols, and olefins). Alternatively, instead of the Lewis acids, organic acids or inorganic acids can be used, and instead of the acid chloride, acid anhydride such as acetic anhydride can be used.

In each step, when an aromatic nucleophilic substitution reaction is performed, examples of the reagents that can be used include nucleophiles (e.g., amines, imidazole) and bases (e.g., basic salts, an organic bases).

In each step, when a nucleophilic addition reaction with a carbanion, a nucleophilic 1,4-addition reaction with a carbanion (Michael addition reaction), or a nucleophilic substitution reaction with a carbanions is performed, examples of the bases to be used in order to generate the carbanion include organolithiums, metal alkoxides, inorganic bases, and organic bases.

In each step, when Grignard reaction is performed, examples of the Grignard reagents include aryl magnesium halides such as phenyl magnesium bromides; and alkyl magnesium halides such as methyl magnesium bromides. The Grignard reagent can be prepared by a method known per se, for example, a method by reacting an alkyl halide or aryl halide with a magnesium metal using an ether or tetrahydrofuran as a solvent.

In each step, when Knoevenagel condensation reaction is performed, example of the reagents that can be used include a compound having active methylene sandwiched between two electron withdrawing groups (e.g., malonic acid, diethyl malonate, or malononitrile) and a base (e.g., organic bases, metal alkoxides, inorganic bases).

In each step, when Vilsmeier-Haack reaction is performed, example of the reagents that can be used include phosphoryl chloride and an amide derivative (e.g., N,N-dimethylformamide).

In each step, when an azidation reaction of alcohols, alkyl halide or sulfonates is performed, examples of the azidation agent to be used include diphenylphosphoryl azide (DPPA), trimethylsilyl azide, and sodium azide. For example, when an azidation of alcohols is performed, a method using diphenylphosphoryl azide and 1,8-diazabicyclo[5,4,0]undec-7-ene (DBU) and a method of using trimethylsilyl azide and a lewis acid can be used.

In each step, when a reductive amination reaction is performed, examples of the reducing agent to be used include sodium triacetoxyborohydride, sodium cyanoborohydride, hydrogen, and formic acid. When the substrate is an amine compound, examples of the carbonyl compound to be used include aldehydes such as paraformaldehyde and acetaldehyde, and ketones such as cyclohexanone. When the substrate is a carbonyl compound, examples of the amine to be used include primary amines such as ammonia and methylamine; and secondary amines such as dimethylamines.

In each step, when a photoextension reaction is performed, examples of the reagent that can be used include azodicarboxylic acid esters (e.g., diethyl azodicarboxylate (DEAD), diisopropyl azodicarboxylate (DIAD), and triphenylphosphine.

In each step, when an esterification reaction, amidation reaction, or ureation reaction is performed, examples of the reagent to be used include acyl halides such as acid chlorides and acid bromides; and activated carboxylic acids such as acid anhydrides, active ester and sulfate esters. Examples of the activators of carboxylic acids include carbodiimide-based condensing agents such as 1-ethyl-3-(3-dimethylaminopropyl) carbodiimide hydrochloride (WSCD); triazine-based condensing agents such as 4-(4,6-dimethoxy-1,3,5-triazin-2-yl)-4-methylmorpholinium chloride-n-hydrochloride (DMT-MM); carbonate-based condensing agents such as 1,1-carbonyldiimidazole (CDI); diphenylphosphate azide (DPPA); benzotriazol-1-yloxy-trisdimethylaminophosphosphonium salt (BOP reagent); 2-chloro-1-methyl-pyridinium iodide (Mukaiyama reagent); thionyl chloride; lower alkyl haloformates such as ethyl chloroformate; O-(7-azabenzotriazol-1-yl)-N,N,N',N'-tetramethyluronium hexafluorophosphate (HATU); 1-(chloro-1-pyrrolidinylmethylene)pyrrolidinium hexafluorophosphate (PyCIU); sulfuric acid; or combinations thereof. When a carbodiimide type condensing agent is used, an additive such as 1-hydroxybenzotriazole (HOBt), and N-hydroxysuccinimide (HOSu), dimethylaminopyridine (DMAP) may be further added to the reaction.

In each step, when a coupling reaction is performed, examples of the metal catalyst to be used include palladium compounds such as palladium(II) acetate, tetrakis(triphenylphosphine) palladium(0), dichlorobis(triphenylphosphine) palladium(II), dichlorobis (triethyl) phosphine palladium(II), tris (dibenzylideneacetone) dipalladium(0), 1,1'-bis(diphenylphosphino)ferrocene palladium(II) chloride, and palladium(II) acetate; nickel compounds such as tetrakis (tri)phenyl phosphine) nickel(0); rhodium compounds such as tris (triphenyl phosphine) rhodium(III) chloride; cobalt compounds; copper compounds such as copper oxide and copper(I)iodide; and platinum compounds. Furthermore, a base may be added to the reaction, and examples of such base include inorganic bases and basic salts.

In each step, when a thiocarbonylation reaction is performed, typical examples of the thiocarbonylating agent that can be used include diphosphorus pentasulfide, but in place of diphosphorus pentasulfide, a reagent having a 1,3,2,4-dithiadiphosphetan-2,4-disulfide structure such as 2,4-bis(4-methoxyphenyl)-1,3,2,4-dithiadiphosphetan-2,4-disulfide (Lowesson's reagent) may be used.

In each step, when Wohl-Ziegler reaction is performed, examples of the halogenating agent to be used include N-iodosuccinimide, N-bromosuccinimide (NBS), N-chlorosuccinimide (NCS), bromine, and sulfuryl chloride. Furthermore, the reaction can be accelerated by adding heat, light, or a radical initiator such as benzoyl peroxide and azobisisobutyronitrile to the reaction.

In each step, when a halogenation reaction of a hydroxy group is performed, examples of the halogenating agents to be used include an acid halide compound of a hydrogen halide acid and an inorganic acid.

Specifically, in the case of chlorination, examples of the acid halide compound include hydrochloric acid, thionyl chloride, or phosphorus oxychloride, and in the case of the bromination, examples of the acid halide compound include 48% hydrobromic acid. Alternatively, a method of obtaining an alkyl halide from an alcohol by the action of, for example, triphenylphosphine and carbon tetrachloride or carbon tetrabromide may be used. Still alternatively, a method of synthesizing an alkyl halide through a two-step reaction including converting the alcohol to a sulfonate, and then reacting the sulfonate with lithium bromide, lithium chloride or sodium iodide may be used.

In each step, when Arbuzov reaction is performed, examples of the reagent to be used include alkyl halides such as ethyl bromoacetate; and phosphites such as triethyl phosphite and tri(isopropyl) phosphite.

In each step, when a sulfone esterification reaction is performed, examples of the sulfonating agent to be used include methanesulfonyl chloride, p-toluenesulfonyl chloride, methanesulfonic anhydride, and p-toluenesulfonic anhydride.

In each step, when a hydrolysis is performed, examples of the reagent that can be used include an acid or base. Also, when an acid hydrolysis of t-butyl ester is performed, formic acid, triethylsilane, and the like may be added to trap secondary-produced t-butyl cations by reduction.

In each step, when a dehydration reaction is performed, examples of the dehydrating agent to be used include sulfuric acid, diphosphorus pentaoxide, phosphorus oxychloride, N,N'-dicyclohexylcarbodiimide, alumina, and polyphosphoric acid.

The compound (1) can be produced by an amidation reaction using compounds (2) and (3).

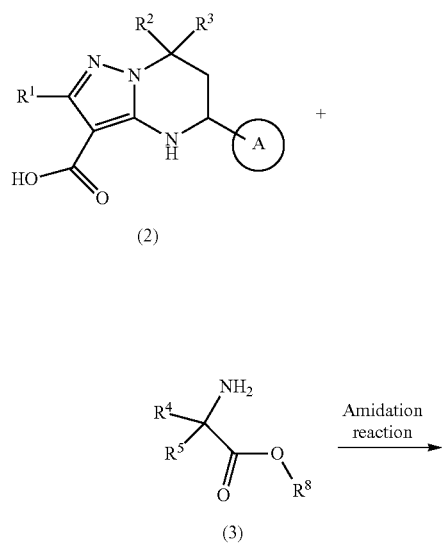

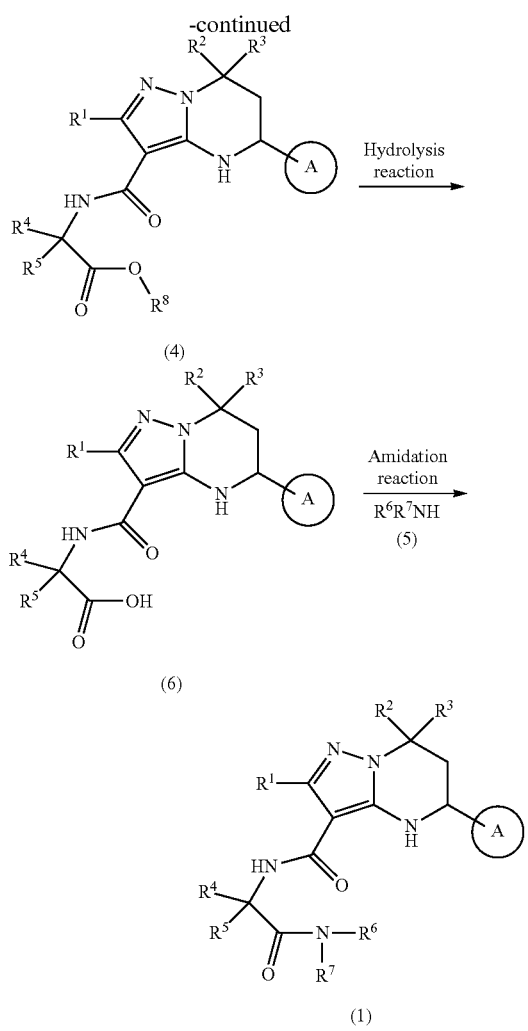

wherein $R^8$ is a protecting group for a carboxyl group, and the other symbols have the same meanings as defined above.

Compounds (2), (3) and (5) each can be a commercially available reagent, or can be produced according to a method known per se.

When compound (I) has an optical isomer, a stereoisomer, a regioisomer, or a rotamer, these can also be included as compound (I), or alternatively each can be obtained as a single product by a synthesis method or a separation method (for example, concentration, solvent extraction, column chromatography, or recrystallization) known per se. For example, when compound (I) has an optical isomer, the optical isomer resolved from the compound is also encompassed as compound (I).

The optical isomers can be produced by a method known per se. Specifically, an optical isomer is obtained by using an optically active synthetic intermediate, or optically resolving the racemate of the final product according to a conventional method.

Examples of the optically resolving method that can be employed include a method known per se, such as a fractional recrystallization method, a chiral column method, or a diastereomer method.

1) Fractional Recrystallization Method

A method by forming a salt of a racemate and an optically active compound (for example, (+)-mandelic acid, (−)- mandelic acid, (+)-tartaric acid, (−)-tartaric acid, (+)-1-phenethylamine, (−)-1-phenethylamine, cinchonine, (−)-cinchonidine, or brucine), separating the salt by a fractional recrystallization method, and as desired, performing a neutralization step to obtain a free optical isomer.

2) Chiral Column Method

A method by separating a racemate or a salt thereof with a column for optical isomer separation (chiral column). For example, when a liquid chromatography is employed, a mixture of optical isomers is added to a chiral column such as ENANTIO-OVM (manufactured by Tosoh Corp.) or CHIRAL series (manufactured by Daicel Chemical Industries Ltd.), and then developed using a solution of water, various buffer solutions (e.g., phosphorus buffer solution) or an organic solvent (e.g., ethanol, methanol, 2-propanol, acetonitrile, trifluoroacetic acid, diethylamine) alone or in a combination to separate the optical isomers. Furthermore, when a gas chromatography is employed, a chiral column such as CP-Chirasil-DeX CB (manufactured by GL Sciences Inc.) is used to separate the optical isomers.

3) Diastereomer Method

A method by converting a mixture of racemates to a mixture of diastereomers by a chemical reaction using an optically active reagent; subjecting the mixture of diastereomers to conventional separation means (e.g., fractional recrystallization, or chromatography) to obtain a single substance; subjecting the substance to a chemical treatment such as a hydrolysis; and cutting off the optically active reagent site to obtain an optical isomer. For example, when compound (I) has a hydroxy or a primary or secondary amino group in the molecule, the compound is subjected to a condensation reaction with an optically active organic acid (e.g., MTPA [α-methoxy-α-(trifluoromethyl)phenylacetic acid], or (−)-menthoxyacetic acid) to obtain each diastereomer of an ester form or an amide form. On the other hand, when the compound has a carboxy group, compound (I) is subjected to a condensation reaction with an optically active amine or alcohol reagent to obtain each diastereomer of an amide form or an ester form. The separated diastereomers are converted to the optical isomers of the original compound by subjecting the diastereomers to acid hydrolysis or basic hydrolysis.

Compound (I) may be a crystal.

The crystal of compound (I) can be produced by crystallizing compound (I) by a crystallization method known per se.

Examples of the crystallization method include a crystallization method from solution, a crystallization method from vapor, and a crystallization method from a melt.

The "crystallization method from solution" is generally a method of transitioning from an unsaturated state to a supersaturated state by changing factors associated with the solubility of the compound (solvent composition, pH, temperature, ionic strength, redox state, etc.) or amount of a solvent. Specific examples of the method include a concentration method, a slow cooling method, a reaction method (a diffusion method, an electrolysis method), a hydrothermal culture method, and a melting agent method. Examples of the solvent that can be used include aromatic hydrocarbons (e.g., benzene, toluene, xylene), halogenated hydrocarbons (e.g., dichloromethane, chloroform), saturated hydrocarbons (e.g., hexane, heptane, cyclohexane), ethers (e.g., diethyl ether, diisopropyl ether, tetrahydrofuran, dioxane), nitriles (e.g., acetonitrile), ketones (e.g., acetone), sulfoxides (e.g., dimethyl sulfoxide), acid amides (e.g., N,N-dimethylformamide), esters (e.g., ethyl acetate), alcohols (e.g., methanol, ethanol, 2-propanol), and water. These solvents may be used alone or in combination of two or more in an appropriate ratio (e.g., 1:1 to 1:100 (volume ratio)). In addition, seed crystals can be used as needed.

Examples of the "crystallization method from vapor" include a vaporization method (a sealing method, an airflow method), a vapor phase reaction method, and a chemical transport method.

Examples of the "crystallization method from a melt" include a normal freezing method (a pulling method, a temperature gradient method, Bridgman method), a zone melting method (a zone leveling method, a float zone method), a special growth method (VLS method, a liquid phase epitaxy method).

Preferable examples of the crystallization method include a method by dissolving a compound (I) in a suitable solvent (e.g., an alcohol such as methanol and ethanol) under a temperature of 20 to 120° C. and cooling the resulting solution to a temperature at dissolution or lower temperature (e.g., 0° C. to 50° C., preferably 0° C. to 20° C.).

The crystals of the present invention thus obtained can be isolated, for example, by filtration.

As an analysis method of the obtained crystals, an analysis method of crystal by powder X-ray diffraction is generally employed. Examples of the method of determining orientation of the crystal include a mechanical method or an optical method.

The crystal of compound (I) obtained by the above production method is expected to be highly pure and high quality, low in hygroscopicity, not deteriorated even if stored for a long time under ordinary conditions, and excellent in stability. The crystal of compound (I) is also excellent in biological properties (e.g., in vivo pharmacokinetics (absorptivity, distribution, metabolism, excretion), and medicinal efficacy) and may be useful as a medicament.

The prodrug of compound (I) refers to a compound that is converted to compound (I) by reaction with an enzyme or gastric acid or the like under physiological conditions in vivo. In other words, the prodrug of compound (I) refers to a compound that undergoes enzymatic oxidation, reduction, hydrolysis or the like to change into compound (I), or a compound that is hydrolyzed by gastric acid or the like to change into compound (I). Examples of the prodrug of compound (I) include a compound in which the amino group of compound (I) is acylated, alkylated or phosphorylated [e.g., a compound in which the amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidyl methylated, pivaloyloxymethylated, or tert-butylated]; a compound in which a hydroxyl group of compound (I) is acylated, alkylated or phosphorylated, and a boronated (e.g., a compound in which the hydroxyl group of compound (I) is acetylated, palmitoylated, propanoylated, pivaloylated, succinylated, fumarylated, alanylated, or dimethylaminomethylcarbonylated); a compound in which the carboxyl group of compound (I) is esterified or amidated [e.g., a compound in which the carboxyl group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, and cyclohexyloxycarbonylethyl esterified, methylamidated]. These compounds can be produced from compound (I) by a method known per se.

The prodrug of compound (I) may also be one that changes into compound (I) under physiological conditions, as described in "Pharmaceutical research and development", volume 7, molecular design, pp. 163-198, 1990, published by Hirokawa-Shoten Ltd.

As used herein, compound (I) and the prodrug of compound (I) are sometimes collectively abbreviated as the "compound of the present invention".

Compound (I) may be a non-solvate or a solvate. The solvent of the solvate may be a solvent such as ethanol or water. When the solvent incorporated is water, the solvate is a hydrate. The hydrate encompasses not only a stoichiometric hydrate, but also a hydrate containing various amounts of water.

Compound (I) may be labeled with isotopes (e.g., $^3$H, $^{13}$C, $^{14}$C, $^{18}$F, $^{35}$S, $^{125}$I) or the like, and compounds labeled or substituted with isotopes can be used, for example, in Positron Emission Tomography (PET) as tracers (PET tracers) and may be useful in the field of medical diagnostics, and the like.

Furthermore, deuterium compounds in which $^1$H is converted to $^2$H(D) are also encompassed in compound (I). Tautomers are also encompassed in compound (I).

Compound (I) may be a pharmaceutically acceptable co-crystal or a co-crystal salt. The co-crystal or co-crystal salt refers to a crystalline substance composed of two or more unique solids at room temperature, each of the solids having different physical properties (e.g., structure, melting point, heat of fusion, hygroscopicity, solubility, and stability). The co-crystal or co-crystal salt can be produced according to a co-crystallization method known per se.

Compound (I) has an excellent antagonistic activity to calcium-sensing receptors.

Compound (I) has low toxicity and can be safely administered to mammals (e.g., humans, rats, mice, dogs, rabbits, cats, cattle, horses, pigs).

Thus, a medicament containing a compound of the present invention is a calcium-sensing receptor antagonist, and is expected to be useful for prevention or treatment of diseases with which the calcium-sensing receptor is associated, such as heart failure; pulmonary hypertension; hyperthyroidism; hypocalcemia; osteoarthropathy (e.g., postmenopausal osteoporosis, senile osteoporosis, secondary osteoporosis, osteomalacia, renal osteodystrophy, fractures, osteoarthritis, rheumatoid arthritis, osteosarcoma, myeloma); and central nervous system diseases.

The use of the compound of the present invention for preventing or treating heart failure will be described in further detail.

The clinical states of heart failure are classified by New York Heart Association (NYHA) into four categories as shown in Table 1, based on severity.

TABLE 1

| NYHA classification of Heart Failure | |
|---|---|
| Class | Patient Symptoms |
| Grade I | Patient has heart disease but there are no limitations of physical activity. Daily physical activity does not cause significant fatigue, palpitation, dyspnea or anginal pain. |
| Grade II | Slight limitation of physical activity. No symptoms when at rest. Daily physical activity causes fatigue, palpitation, dyspnea or anginal pain. |

TABLE 1-continued

| NYHA classification of Heart Failure | |
|---|---|
| Class | Patient Symptoms |
| Grade III | Marked limitations of physical activity. No symptoms when at rest. Less than ordinary physical activity causes fatigue, palpitation, dyspnea or anginal pain. |
| Grade IV | All physical activity is limited due to heart disease. Heart failure symptoms or anginal pain even when at rest. These symptoms worsen even with slight exertion. |

* Grade IIs: Slight limitation of physical activity
Grade IIm: Moderate limitation of physical activity The clinical states are also classified according to AHA/ACC (American Heart Association/American College of Cardiology) stage classification into four categories as shown in Table 2, based on severity.

TABLE 2

| AHA/ACC stage classification of Heart Failure | |
|---|---|
| Stage | Definition |
| A | Patients at risk for heart failure but no cardiac dysfunction |
| B | Patients with asymptomatic, left ventricular systolic dysfunction |
| C | Patients who have developed symptomatic heart failure |
| D | Patients with refractory heart failure requiring advanced intervention |

The correspondence relation between the NYHA classification and the AHA/ACC stage classification is generally considered as shown in the following Table 3.

TABLE 3

| Correspondence relation between NYHA classification and AHA/ACC stage classification | |
|---|---|
| NYHA classification | AHA/ACC stage classification |
| — | A |
| Grade I | B |
| Grade II | C |
| Grade III | |
| Grade IV | |
| Grade IV | D |

The compound of the present invention is used as an agent for preventing or treating heart failure, reduction of cardiac output, ischemic heart failure or non-ischemic heart failure, decompensated heart failure, acute heart failure, and acute decompensated heart failure, as determined by the aforementioned reports.

The compound of the present invention can also be used to improve reduction of ejection fraction or increase ejection fraction in a subject having heart failure.

Furthermore, the compound of the present invention can also suppress the cardiac function deterioration or suppress the progression of deterioration in a subject having heart failure. The compound of the present invention can also reduce burden on the heart, can suppress cardiac hypertrophy, can suppress interstitial fibrosis, and can suppress an increase in apoptosis in a subject having heart failure.

The use of the compound of the present invention for preventing or treating pulmonary hypertension will be described in further detail.

The criteria for determining pulmonary hypertension are described, for example, in the Guideline for the Treatment of Pulmonary Hypertension (Revised, 2012) by the Japanese Circulation Society.

The diagnosis of pulmonary hypertension in humans is usually made based on mean pulmonary artery pressure (mean PAP) measured by right heart catheterization at rest, and the diagnosis of pulmonary hypertension may be made if the mean pulmonary artery pressure is 25 mmHg or more. Developments in cardiac echocardiography in recent years have made it possible to noninvasively estimate pulmonary arterial pressure, and diagnoses of pulmonary hypertension are sometimes conducted based on pulmonary arterial pressure estimates.

Pulmonary hypertension is clinically classified into five groups of group 1 to group 5 by Dana point classification. The group 1 is pulmonary arterial pulmonary hypertension (PAH), the group 2 is pulmonary hypertension with left ventricular heart disease, the group 3 is pulmonary hypertension with pulmonary disease and/or hypoxemia, the group 4 is chronic thromboembolic pulmonary hypertension, and the group 5 is pulmonary hypertension due to a combination of unspecified factors. As subtypes of the group 1, group 1' (pulmonary venous embolic disease and/or pulmonary capillary angiomatosis) and group 1" (neonatal progressive pulmonary hypertension) are known.

Pulmonary arterial pulmonary hypertension in the group 1 is the most typical pulmonary hypertension and is roughly classified into spontaneous PAH, hereditary PAH, drug/toxicant-induced PAH, and PAH associated with each disease.

The compound of the present invention can be used as an agent for preventing or treating pulmonary hypertension, as determined by the aforementioned reports. The compound of the present invention can also ameliorate various symptoms (such as elevated right ventricular pressure) associated with pulmonary hypertension, for example, by lowering pulmonary arterial pressure, in a subject.

The compound of the present invention can be used for preventing or treating heart diseases such as cardiomyopathy and arrhythmia.

The compound of the present invention can be used for cardiomyopathies described below as an agent for preventing or treating myocardial hypertrophy, myocardial remodeling, cardiomyocyte injury, occurrence of arrhythmia, cardiac pump dysfunction or sudden death.

There are several classifications of cardiomyopathy, which are defined by proposals of (i) WHO/ISFC (1995), (ii) the American Heart Association (AHA, 2006), (iii) European Society of Cardiology (ESC, 2008), for example. Details of the type of cardiomyopathy are shown below.

(i) Proposals of WHO/ISFC at 1995 (Table 4)

In the WHO/ISFC (1995) proposal, cardiomyopathies are defined as "diseases of the myocardium associated with cardiac dysfunction". Based on the clinical condition, the cardiomyopathies are classified into the types of 1) dilated cardiomyopathy, 2) hypertrophic cardiomyopathy, 3) restrictive cardiomyopathy, 4) arrhythmogenic right ventricular cardiomyopathy, and 5) unclassified cardiomyopathy. In addition, myocardial diseases that have a specific cause or are clearly associated with causes or systemic diseases are classified as specific cardiomyopathy. Examples of the specific cardiomyopathy include cardiomyopathy associated with ischemia (such as angina, myocardial infarction), valve disease (such as valvular heart disease), hypertension, inflammatory (such as infectious, myocarditis), metabolism (such as thyroid dysfunction, endocrine diseases such as adrenocortical dysfunction, amyloidosis, nutritional disorders, glycogen storage disease, hereditary metabolic abnormalities such as Fabry's disease), hypersensitivity/intoxication (such as alcoholic cardiomyopathy, medicinal, radiological), puerperium (such as pregnancy and childbirth dysregulation), myodystrophy (such as ankylosing muscle atrophy), neurological and muscular diseases (such as Noonan's syndrome, Friedrich's ataxia), and systemic diseases (such as collagen disease, sarcoidosis, rheumatoid arthritis, scleroderma).

TABLE 4

Definition and classification into type of Cardiomyopathies by 1995 WHO/ISFC Task Force Definition: Cardiomyopathies refer to diseases of myocardium associated with cardiac dysfunction
Classification 1. dilated cardiomyopathy (DCM)
2. hypertrophic cardiomyopathy (HCM)
3. restrictive cardiomyopathy (RCM)
4. arrhythmogenic right ventricular cardiomyopathy
5. unclassified cardiomyopathy
specific cardiomyopathies Circulation 1996, 93 841-842, modified (cited from "guidelines for diagnosis and treatment of patients with hypertrophic cardiomyopathy" (2012, revised version))

(ii) Proposal of the American Heart Association (AHA, 2006) (Table 5)

According to the proposal of AHA (2006), cardiomyopathy is defined as "a heterogeneous group of diseases of the myocardium associated with mechanical or electrical dysfunction that usually exhibit inappropriate ventricular hypertrophy or dilatation and are due to a variety of causes that frequently are genetic." (Definitions and Classification of Cardiomyopathies (AHA proposal) (Table 5)). Based on the site of the lesion, cardiomyopathy is divided into primary cardiomyopathy in which the lesion is predominantly confined to heart; and secondary cardiomyopathy in which the myocardial lesions are involved in systemic disease. Furthermore, primary cardiomyopathy is classified into three types of hereditary, acquired and a mixed type of these. Examples of the hereditary type include hypertrophic cardiomyopathy, arrhythmogenic right ventricular cardiomyopathy, left ventricular noncompaction, glycogen strage disease (PPKA2, Danon's disease), conduction abnormalities, mitochondrial cardiomyopathy, ionic channel disorders (Long QT syndrome, Burgata syndrome, Short QT syndrome, catecholaminergic polymorphic ventricular tachycardia, and Asian SUNDS (nocturnal sudden death syndrome)). Examples of the acquired type include inflammatory cardiomyopathy (myocarditis), stress-induced cardiomyopathy (Takotsubo cardiomyopathy), postpartum cardiomyopathy, tachycardia-induced cardiomyopathy, and cardiomyopathy of an infant born from an insulin-dependent mother. Examples of the mixed type include dilated cardiomyopathy and restrictive cardiomyopathy (left ventricular hypertrophy without enlargement).

Figure 2:
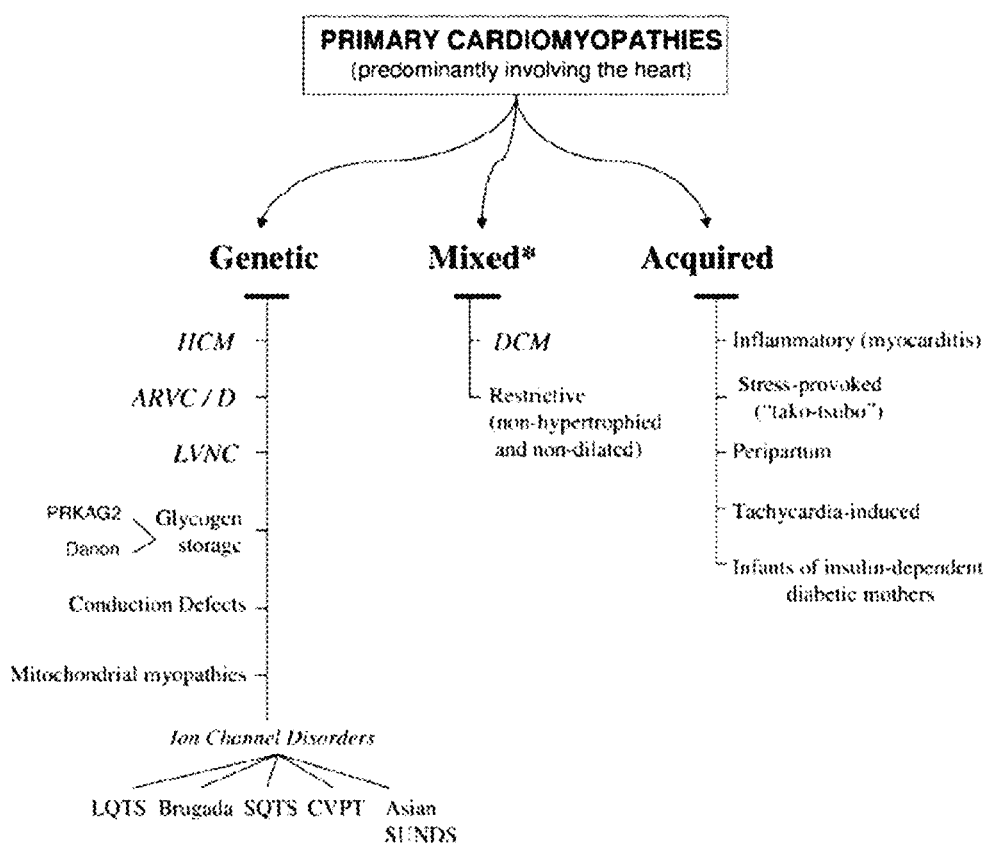
FIG. 2 shows Table 5, which illustrates the Definitions and Classifications of Cardiomyopathies in the AHA proposal.

[Table 5] See FIG. 2.

(iii) Proposal of the European Society of Cardiology (ESC, 2008) (Table 6)

The proposal of ESC (2008) defines cardiomyopathy as "A myocardial disorder in which the heart muscle is structurally and functionally abnormal, in the absence of coronary artery disease, hypertension, valvular disease and congenital heart disease sufficient to cause the observed myocardial abnormality" (Table 6). Similar to WHO/ISFC classification, cardiomyopathy is classified into 5 major types of 1) dilated cardiomyopathy, 2) hypertrophic cardiomyopathy, 3) restrictive cardiomyopathy, 4) arrhythmogenic right ventricular cardiomyopathy, and 5) unclassified cardiomyopathy. Similar to the AHA classification, the concept of genetic/non-genetic has been introduced and these diseases have been classified into two groups of familial/genetic and non-familial/non-genetic.

Figure 3:
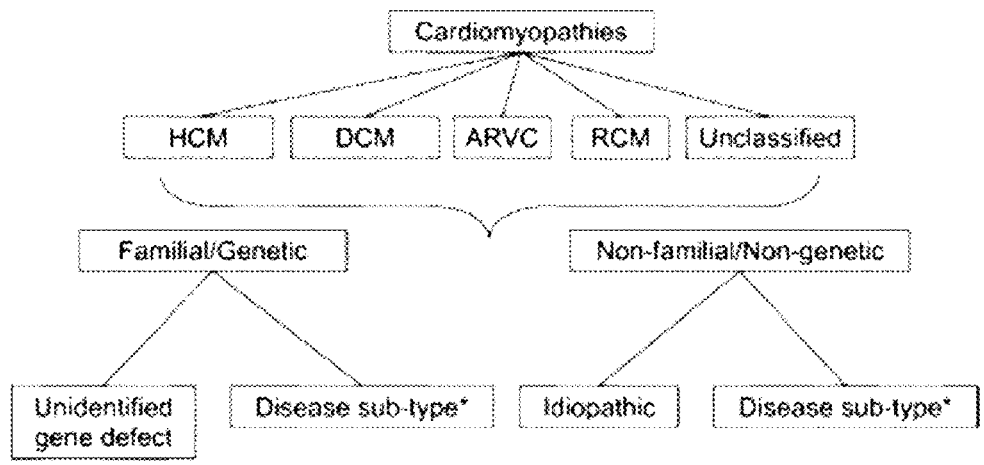
FIG. 3 shows Table 6, which illustrates the Definitions and Classifications of Cardiomyopathies in the ESC proposal.

[Table 6] See FIG. 3.

The compound of the present invention can be used as an agent for preventing or treating arrhythmia shown below including the occurrence of arrhythmia, or sudden death with arrhythmia.

Arrhythmia is, in terms of symptoms, roughly divided into bradyarrhythmia and tachyarrhythmia. The generation mechanism of arrhythmia is considered as (i) stimulation generation abnormality and (ii) stimulation conduction abnormality (excitation conduction abnormality), which are mainly due to cardiac disorders. When cardiac muscle is impaired by a variety of causes (genetic predisposition, environmental stress, or the like), the sites where electrical signals are easily transmitted or where abnormal excitation occurs are generated in the cardiac muscle locally, resulting in arrhythmias.

Arrhythmia is also classified according to the generation mechanism (cause) as follows.

(i) Types of Arrhythmias Due to Stimulation Generation Abnormality and their Main Causes Sinus bradycardia (mainly caused by myocardial infarction; sick sinus syndrome; hypothyroidism; jaundice (severe); drugs such as digoxin, beta blockers, and calcium antagonists; intracranial hypertension; idiopathy; or the like)

Atrial premature contraction (mainly caused by hypertensive heart disease; angina pectoris; myocardial infarction; valvular heart disease; cardiomyopathy; myocarditis; heart failure; congenital heart disease; pulmonary disease; hyperthyroidism; drugs such as bronchodilator agents and catecholamines; idiopathy; or the like)

Paroxysmal supraventricular tachycardia (mainly caused by hyperthyroidism; hypertensive heart disease; drugs such as atropine; idiopathy; or the like)

Atrial fibrillation (mainly caused by mitral valve stenosis; hyperthyroidism; ischemic heart disease; elevated intraatrial pressure; hypoxemia; sinus failure syndrome; cardiomyopathy; pulmonary disease: idiopathy (isolated); or the like)

Atrial flutter (mainly caused by mitral or tricuspid valve disease; cor pulmonale; coronary artery disease; cardiomyopathy; myocarditis; hyperthyroidism; electrolyte abnormality; drugs such as catecholamine; idiopathy; or the like)

Atrioventricular junction rhythm (mainly caused by acute myocardial infarction; the other ischemic heart disease; hypertension; myocarditis; idiopathy; or the like)

Ventricular extrasystole (mainly caused by acute myocardial infarction; cardiomyopathy; idiopathy; or the like)

Ventricular fibrillation (mainly caused by acute myocardial infarction; cardiomyopathy; WPW syndrome; Long QT syndrome; Burgata syndrome, catecholaminergic polymorphic ventricular tachycardia; idiopathy; or the like)

Ventricular tachycardia (mainly caused by acute myocardial infarction; cardiomyopathy; valvular heart disease; idiopathy; or the like)

(ii) Types of Arrhythmias Due to Stimulation Conduction Abnormality and their Main Causes Bradycardic atrial fibrillation (mainly caused by digitalis poisoning; idiopathy; or the like)

Sick sinus syndrome (mainly caused by aging; coronary artery disease; drugs such as quinidine and digoxin; idiopathy; or the like)

Sinoatrial block (mainly caused by myocardial infarction; coronary artery occlusion; drugs such as digoxin, anti-arrhythmic drugs, beta blockers, and calcium antagonists; idiopathy; or the like)

Atrioventricular block (mainly caused by acute myocardial infarction; valvular heart disease; cardiomyopathy; drugs such as digoxin and beta blockers; aging; congenital; idiopathy; or the like)

Bundle branch block (mainly caused by hypertensive heart diseases; myocardial infarction; cardiomyopathy; leg injury caused by cardiac surgery; congenital; idiopathy; or the like)

Ventricular premature contraction (mainly caused by digitalis poisoning, myocardial infarction, cardiomyopathy, electrolyte abnormality, idiopathy; or the like)

Among these arrhythmic diseases, there are diseases in particular characterized by genetic abnormalities of myocardial ion channels or the like. These diseases are a group of intractable diseases which develop fatal arrhythmias and cause sudden death in relatively young generations. Thus, effective prevention and treatment of these diseases can be expected to not only improve patients' QOL but also provide socioeconomic effects. Examples of hereditary arrhythmias include congenital long QT syndrome, short QT syndrome, burgata syndrome, catecholaminergic polymorphic ventricular tachycardia, progressive cardiac conduction defects (familial cardiac block), congenital sick sinus syndrome, familial atrial fibrillation, arrhythmogenic right ventricular cardiomyopathy, acquired long QT syndrome, and early repolarization syndrome.

In a certain aspect of the present invention, the medicament of the present invention can be used to prevent and treat pulmonary hypertension selected from pulmonary hypertension: pulmonary arterial pulmonary hypertension; pulmonary hypertension due to pulmonary venous embolic disease; pulmonary hypertension due to pulmonary capillary hemanqiomatosis; persistent neonatal pulmonary hypertension; left ventricular systolic failure, left ventricular dysplasia, valve disease, or pulmonary hypertension with congenital/acquired left cardiac inflow/outflow channel occlusion; chronic obstructive pulmonary disease, interstitial pulmonary disease, other pulmonary disease with high velocity and occlusive mixed disorders, sleep breathing disorder, pulmonary hypoventilation disorder, chronic exposure at height, or pulmonary hypertension due to developmental disorder; chronic thromboembolic pulmonary hypertension; hematological diseases (chronic hemolytic anemia, myeloproliferative disease, or splenectomy), systemic disease (sarcoidosis, pulmonary Langerhans cell histiocytosis, lymphangiomyoma, neurofibromatosis, or vascular inflammation), metabolic disease (glycogen storage disease, Gaucher disease, or thyroid disease), and the other pulmonary hypertension accompanying with pulmonary vascular compression (tumor embolism, fibrotic mediastinitis, or chronic renal failure). The medicament of the present invention is preferably used for the prevention or treatment of pulmonary arterial pulmonary hypertension.

In a further specific aspect of the present invention, the medicament of the present invention is a medicament for improving one or more conditions selected from the group consisting of right ventricular pressure, right ventricular contraction pressure, survival rate, and cardiac hypertrophy in a subject having pulmonary hypertension.

The medicament of the present invention comprises a compound represented by formula (I) or a salt thereof. A medicament of the present invention may further comprise a pharmaceutically acceptable carrier, and optionally a formulation additive as needed.

As the pharmaceutically acceptable carrier, various organic or inorganic carrier substances conventionally used as pharmaceutical ingredients are used. Examples of such carrier substances include an excipient, a lubricant, a binder, or a disintegrant in solid preparations; and a solvent, a suspending agent, a tonicity agent, a buffering agent, or a soothing agent in liquid preparations. Optionally, a formulation additive such as a preservative, an antioxidant, a stabilizer, a colorant, or a sweetener can also be used as needed.

The medicament of the present invention can be, in one aspect, a medicament for parenteral administration or oral administration.

The medicament for oral administration may be any of solid preparations such as powders, granules, tablets or capsules, or Jiquid preparations such as syrups or emulsions.

The medicament of the present invention can be manufactured by conventional methods such as mixing, kneading, granulation, tableting, coating, sterilization, or emulsification depending on the form of preparation. Regarding manufacture of the preparations, for example, respective items of General Rules for Preparations in the Japanese Pharmacopoeia can be referred. The medicament of the present invention may also be formulated into a sustained-release agent comprising the active ingredient and a biodegradable polymeric compound.

The dose varies depending on administration subject, administration route, disease, symptoms, and the like. For example, when the medicament of the present invention is administered for the purpose of treating heart failure or pulmonary hypertension, for oral administration to human (about 50 kg bodyweight), the dose can be selected from the range of about 0.1 mg to about 500 mg, preferably the range of about 1 mg to about 100 mg in terms of compound (I); and for parenteral administration, the dose can be selected from the range of about 0.01 mg to about 100 mg, preferably about 0.1 mg to about 10 mg in terms of compound (I). The dose can be administered in single or divided doses of one to several times a day (e.g., one to three times a day).

The medicament of the present invention can be used in combination with other drugs (combination drugs).

In a certain aspect of the present invention, the medicament of the present invention is used in combination with other medicaments for the purpose of treating or preventing heart failure. Examples of the other medicaments that can be used include any one or more of the following medicaments:

(1) Heart Failure Therapeutic Drugs
 (i) beta receptor antagonists: carvedilol, metoprolol, atenolol;
 (ii) diuretics: hydrochlorothiazide, spironolactone, furosemide, indapamide, bendroflurazide, cyclopentiazide, bumetanide, ethacrylic acid;
 (iii) cardiotonics: digoxin, dobutamine;
 (iv) anti-aldosterone drugs: spironolactone, eplerenone;
 (v) heart rate lowering drugs: ivabradine;
 (vi) intravenous cardiotonics: h-ANP;
 (vii) others: relaxin;

(2) Others
 (viii) Ca sensing enhancing drugs: MCC-135;
 (ix) Ca channel antagonists: nifedipine, diltiazem, verapamil, lomerizine hydrochloride, amlodipine besylate;
 (x) antiplatelets, anticoagulants: heparin, aspirin, warfarin, dabigatran, rivaroxaban, pixaban, edoxaban;
 (xi) HMG-CoA reductase inhibitor: atorvastatin, simvastatin;
 (xii) uric acid lowering drugs: probenecid, alloprinol, febuxostat;
 (xiii) alpha blockers: doxazosin;
 (xiv) oral adsorbents: cremezin;
 (xv) high potassium plasma therapeutics: calcicol;
 (xvi) high phosphorus plasma therapeutics: sevelamer, lanthanum carbonate;
 (xvii) metabolic acidosis improving drugs: sodium bicarbonate;
 (xviii) the others: active vitamins.

In another aspect of the present invention, the medicament of the present invention is a medicament for preventing or treating pulmonary hypertension in a subject in need thereof. The medicament of the present invention comprises compound (I), and may be used in combination with other drugs (combination drugs).

In a specific aspect of the present invention, the medicament of the present invention is used in combination with other medicaments for the purpose of treating or preventing pulmonary hypertension. Examples of the other medicaments that can be used include any one or more of the following medicaments:

(i) endothelin receptor antagonists: endothelin receptor antagonists such as masitentan, bosentan, and ambrisentan;
(ii) prostaglandin formulations: prostaglandin formulations (or prostacyclin formulations) such as epoprostenol, velaprost, treprostinyl, iroprost, and selexipag;
(iii) phosphodiesterase-5 inhibitors: phosphodiesterase-5 inhibitors such as sildenafil and tadalafil;
(iv) soluble adenylate cyclase stimulants: soluble adenylate cyclase stimulants such as riociguat;
(v) calcium channel antagonists: calcium channel antagonists such as nifedipine, diltiazem, and amlodipine;
(vi) Rho kinase inhibitors: Rho kinase inhibitors such as fasudil;
(vii) the others: tyrosine kinase inhibitors such as imatinib and sorafenib; anticoagulants such as warfarin and aspirin; diuretics such as furosemide and spironolactone; and cardiac stimulants such as dopamin and digoxin.

Examples of the medicaments in which the medicament of the present invention and other drug are used in combination or the medicament obtained by formulating the medicament of the present invention with other drug include both a medicament in which compound (I) and a combination drug are formulated into a single agent as a medicament containing compound (I) and the combination drug, and a medicament in which compound (I) and a combination drug are formulated into separate agents. Hereinafter, these are collectively referred to as the combination medicament of the present invention.

The combination medicament of the present invention can be formulated in the same way as those of the medicament containing compound (I) described above, by mixing compound (I) and the combination drug separately or simultaneously, each employed alone or together with a pharmaceutically acceptable carrier, or the like.

The daily dose of the combination medicament of the present invention varies depending on the degree of symptoms; age, sex, bodyweight, sensitivity difference of the subject to be administered; timing and interval of administration; nature, formulation, type of medicament, type of active ingredient; and the like, and it is not particularly limited.

When administering the combination medicament of the present invention, compound (I) and the combination drug may be administered at the same time; and the combination drug is administered, and then, compound (I) or a salt thereof may be administered; or compound (I) or a salt thereof is administered, and then the combination drug may be administered. When the combination medicament is administered with a time difference, the time difference varies depending on the active ingredient to be administered, dosage form, and the administration method. For example, when the combination drug is administered in advance, example of the method include a method administering compound (I) or a salt thereof within 1 minute to 3 days, preferably within 10 minutes to 1 day, more preferably within 15 minutes to 1 hour after the combination drug is administered. When compound (I) is administered in advance, examples of the method include a method of administering the combination drug within 1 minute to 1 day, preferably within 10 minutes to 6 hours, more preferably within 15 minutes to 1 hour after the ingredient is administered.

For the combination medicament of the present invention in which compound (I) and the combination drug are contained together in an agent, the contents of compound (I) and the combination drug each vary depending on the form of the formulation, but usually are about 0.01 to 90% by weight, preferably about 0.1 to 50% by weight, and furthermore preferably about 0.5 to 20% by weight relative to the whole formulation.

The content of the carrier in the combination medicament of the present invention is typically about 0 to 99.8% by weight, preferably about 10 to 99.8% by weight, and furthermore preferably about 10 to 90% by weight relative to the whole formulation.

For the combination medicament of the present invention in which compound (I) or a salt thereof and the combination drug are contained in separate agents, the combination medicament containing the combination drug can be prepared and used in the same way as compound (I) or a salt thereof.

The invention relating to the compounds and the medicaments of the present invention can be converted into inventions of other embodiments such as a method for preventing or treating a disease, and a use of the compound in manufacture of a medicament.

In a certain aspect of the present invention, there is provided a method for preventing or treating heart failure in a subject in need thereof, comprising administering compound (I) to the subject.

In a certain aspect of the present invention, there is provided a use of compound (I) in the manufacture of a medicament for preventing or treating heart failure in a subject in need thereof.

In a certain aspect of the present invention, there is provided a method for preventing or treating pulmonary hypertension in a subject in need thereof, comprising administering compound (I) to the subject.

In a particular aspect of the present invention, there is provided a use of compound (I) for the manufacture of a medicament for preventing or treating pulmonary hypertension in a subject in need thereof.

These technical matters relating to the method of the present invention, such as diseases and conditions to be treated, may be the same as those described above for the medicament of the present invention. In the method of the present invention, when compound (I) is administered, a medicament comprising compound (I) or a salt thereof may be administered instead.

EXAMPLES

The present invention will be described in further detail with the following Examples, Test examples and Formulation examples, but these examples are not limitations of the present invention and may be varied to the extent that they do not depart from the scope of the invention.

In the following examples, "room temperature" usually refers to about 10° C. to about 35° C. The ratio indicated for the mixed solvent denotes volume ratio unless otherwise specified. % indicates % by weight unless otherwise specified.

In Examples, elution in column chromatography was observed by TLC (thin layer chromatography) unless specifically mentioned. In the TLC observation, 60 $F_{254}$ manufactured by Merck was used as the TLC plate, and eluting solvents used in column chromatography were used as the developing solvents. For detection, a UV detector was employed. In silica gel column chromatography, the description NH means that the aminopropylsilane-bonded silica gel was used, and the description Diol means that the 3-(2,3-dihydroxypropoxy) propylsilane-bonded silica gel was used. In preparative HPLC (high performance liquid chromatography), the description C18 means that the octadecyl-bonded silica gel was used. The ratios indicated for the elution solvent denotes volume ratios unless otherwise specified.

The analysis of $^1$H NMR was performed using ACD/SpecManager (trade name) software or the like. Very broad peaks such as proton peaks of hydroxyl and amino groups may not be described.

MS was measured by LC/MS. For ionization, ESI method or APCI method was used. The data are indicated by measured values (Found). The peaks observed are usually molecular ion peaks, but sometimes fragment ions peaks. For salts, the peaks observed are usually molecular ion peaks of free form or fragment ion peaks.

The concentration unit (c) of sample in optical rotation ($[\alpha]_D$) is g/100 mL.

Elemental analysis values (Anal.) are indicated by calculated values (Calcd) and measured values (Found).

The powder X-ray diffraction peaks in Examples indicate peaks measured at room temperature by Ultima IV (Rigaku Corporation, Japan) using Cu Kα radiation as a radiation source. The measurement conditions were as follows.

Electric pressure/Electric current: 40 kV/50 mA
Scan speed: 6 degree/min
Scan range of 2 Theta: 2-35 degree The degree of crystallinity by powder X-ray diffraction in Examples was calculated by Hermans method.

The following abbreviations are used in Examples.
mp: melting point
MS: mass spectrum
M: molar concentration
N: normality
$CDCl_3$: Deuterated chloroform
DMSO-$d_6$: deuterated dimethyl sulfoxide
$^1$H NMR: proton nuclear magnetic resonance LC/MS: liquid chromatograph mass spectrometer
ESI: electrospray ionization
APCI: atmospheric pressure chemical ionization
PyCIU: 1-(Chloro-1-pyrrolidinylmethylene)pyrrolidinium hexafluorophosphate
HATU: (dimethylamino)-N,N-dimethyl(3H-[1,2,3]triazolo[4,5-b]pyridin-3-yloxy)methaniminium hexafluorophosphate
DIPEA: N-ethyl-N-isopropyl propan-2-amine
DMA: N,N-dimethyl acetamide
DMF: N,N-dimethyl formamide
THF: tetrahydrofuran Example 1

(5R)—N-((2R)-1-(((2S)-1-Amino-1-oxopropan-2-yl)amino)-2-(4-ethylphenyl)-1-oxobutan-2-yl)-2,7,7-trimethyl-5-phenyl-4,5,6,7-tetrahydropyrazolo[1,5-a]pyrimidine-3-carboxamide A) Methyl (2R)-2-amino-2-(4-ethylphenyl)butanoate Methyl 2-amino-2-(4-ethylphenyl)butanoate (44.9 g) was fractionated by SFC(CHIRALPAK IC (trade name), 30 mmID×250 mmL), mobile phase: carbon dioxide/(methanol/diethylamine=1000/3)=900/100 (v/v)), and the fraction having shorter retention time was concentrated. To the residue, ethyl acetate and water were added, and the obtained mixture was extracted with ethyl acetate. The organic layer was separated, washed with saturated brine, then dried over anhydrous magnesium sulfate, and then concentrated under reduced pressure to yield the title compound (18.2 g).
Optical purity: >99.9% e.e.
One having shorter retention time under the following optical analysis condition
Column: CHIRALPAK IC (trade name) 4.6 mmID×150 mmL Mobile phase: carbon dioxide/(methanol/diethylamine=1000/3)=900/100 (v/v)
$^1$H NMR (300 MHz, DMSO-$d_6$) δ 0.74 (3H, t, J=7.4 Hz), 1.16 (3H, t, J=7.6 Hz), 1.73-2.09 (2H, m), 2.17 (2H, s), 2.57 (2H, q, J=7.6 Hz), 3.59 (3H, s), 7.15 (2H, d, J=8.4 Hz), 7.30-7.40 (2H, m).

B) Methyl (2R)-2-(4-ethylphenyl)-2-((((5R)-2,7,7-trimethyl-5-phenyl-4,5,6,7-tetrahydropyrazolo[1,5-a]pyrimidin-3-yl)carbonyl)amino)butanoate To a mixture of methyl (2R)-2-amino-2-(4-ethylphenyl)butanoate (233 mg), DIPEA (299 mg) and DMA (3 ml), PyCIU (385 mg) was added at 0° C. Then, a solution of (5R)-2,7,7-trimethyl-5-phenyl-4,5,6,7-tetrahydropyrazolo[1,5-a]pyrimidine-3-carboxylic acid (300 mg) in DMA (1 mL) was added dropwise at 0° C. and the mixture was stirred at 60° C. for 2 hours. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate). The obtained fraction was concentrated under reduced pressure, and purified again by silica gel column chromatography (NH, hexane/ethyl acetate) to yield the title compound (332 mg).
MS: [M+H]$^+$ 489.2.

C) (2R)-2-(4-Ethylphenyl)-2-((((5R)-2,7,7-trimethyl-5-phenyl-4,5,6,7-tetrahydropyrazolo[1,5-a]pyrimidin-3-yl)carbonyl)amino)butanoic acid A mixture of methyl (2R)-2-(4-ethylphenyl)-2-((((5R)-2,7,7-trimethyl-5-phenyl-4,5,6,7-tetrahydropyrazolo[1,5-a]pyrimidin-3-yl)carbonyl)amino)butanoate (10.2 g), THF (100 mL), methanol (100 mL) and 8 M aqueous solution of sodium hydroxide (100 mL) was stirred at 50° C. for 2 hours. The reaction mixture was acidified with 6 M hydrochloric acid at 0° C. and extracted with ethyl acetate. The organic layer was separated, washed with saturated brine, then dried over anhydrous magnesium sulfate, and then concentrated under reduced pressure to yield the title compound (10.2 g).
MS: [M+H]$^+$ 475.2.

D) (5R)—N-((2R)-1-(((2S)-1-Amino-1-oxopropan-2-yl)amino)-2-(4-ethylphenyl)-1-oxobutan-2-yl)-2,7,7-trimethyl-5-phenyl-4,5,6,7-tetrahydropyrazolo[1,5-a]pyrimidine-3-carboxamide To a mixture of (2R)-2-(4-ethylphenyl)-2-((((5R)-2,7,7-trimethyl-5-phenyl-4,5,6,7-tetrahydropyrazolo[1,5-a]pyrimidin-3-yl)carbonyl)amino)butanoic acid (8.47 g), L-alaninamide hydrochloride (2.67 g) and DMF (85 ml), HATU (8.14 g) and DIPEA (6.92 g) was added at 0° C. The mixture was stirred at 70° C. overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate, then ethyl acetate/methanol). The obtained fraction was concentrated under reduced pressure, and the residue was purified by silica gel column chromatography (NH, hexane/ethyl acetate) to yield the title compound (5.24 g) as a noncrystalline solid.
The title compound (5.93 g) obtained by the above method was purified again by silica gel column chromatography (NH, hexane/ethyl acetate). The obtained fraction was concentrated under reduced pressure, and the residue was crystallized with ethyl acetate/diethyl ether. The mixture was concentrated under reduced pressure, and then recrystallized with ethyl acetate/hexane to yield the title compound (3.72 g) as crystals.
$^1$H NMR (300 MHz, DMSO-$d_6$) δ 0.77 (3H, t, J=7.2 Hz), 1.06 (3H, d, J=7.2 Hz), 1.16 (3H, t, J=7.6 Hz), 1.45 (3H, s), 1.47 (3H, s), 1.94-2.15 (2H, m), 2.44 (3H, s), 2.52-2.77 (4H, m), 4.07-4.21 (1H, m), 4.61 (1H, dd, J=11.1, 3.2 Hz), 6.28 (1H, s), 6.98 (1H, s), 7.14 (2H, d, J=8.3 Hz), 7.20-7.44 (8H, m), 7.50 (1H, d, J=7.4 Hz), 7.61 (1H, s).

Example 2

(5R)—N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide A) Methyl 2-((((5R)-7,7-dimethyl-5-phenyl-4,5,6,7-tetrahydropyrazolo[1,5-a]pyrimidin-3-yl)carbonyl)amino)-2-(4-ethylphenyl)butanoate A mixture of (5R)-7,7-dimethyl-5-phenyl-4,5,6,7-tetrahydropyrazolo[1,5-a]pyrimidine-3-carboxylic acid (1.655 g), HATU (2.78 g), DIPEA (0.079 mL) and DMF (15 mL) was stirred at room temperature for 5 minutes. Then, a mixture of methyl 2-amino-2-(4-ethylphenyl)butanoate (1.35 g) and DMF (5 ml) was added, and the mixture was stirred at 80° C. overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate) to yield the title compound (1.50 g).

MS: $[M+H]^+$ 475.2.

B) 2-(((((5R)-7,7-Dimethyl-5-phenyl-4,5,6,7-tetrahydropyrazolo[1,5-a]pyrimidin-3-yl)carbonyl)amino)-2-(4-ethylphenyl)butanoic acid A mixture of methyl 2-(((((5R)-7,7-dimethyl-5-phenyl-4,5,6,7-tetrahydropyrazolo[1,5-a]pyrimidin-3-yl)carbonyl)amino)-2-(4-ethylphenyl)butanoate (1.45 g), THF (10 ml), methanol (10 mL) and 8 M aqueous solution of sodium hydroxide (10 mL) was stirred at 75° C. for 1 hour. The mixture was acidified with 6 M hydrochloric acid at 0° C., and extracted with ethyl acetate. The organic layer was separated, washed with saturated brine, then dried over anhydrous magnesium sulfate, and then concentrated under reduced pressure to yield the title compound (1.40 g).

MS: $[M+H]^+$ 461.2.

C) (5R)—N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide A mixture of 2-(((((5R)-7,7-dimethyl-5-phenyl-4,5,6,7-tetrahydropyrazolo[1,5-a]pyrimidin-3-yl)carbonyl)amino)-2-(4-ethylphenyl)butanoic acid (331 mg), L-alaninamide hydrochloride (107 mg), HATU (328 mg), DIPEA (279 mg) and DMF (4 ml) was stirred at room temperature overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate) to yield the title compound (217 mg).

Example 3

5R)—N-((2S)-1-(((2S)-1-Amino-1-oxopropan-2-yl)amino)-2-(4-ethylphenyl)-1-oxobutan-2-yl)-2,7,7-trimethyl-5-phenyl-4,5,6,7-tetrahydropyrazolo[1,5-a]pyrimidine-3-carboxamide A) Methyl 2-(4-ethylphenyl)-2-(((((5R)-2,7,7-trimethyl-5-phenyl-4,5,6,7-tetrahydropyrazolo[1,5-a]pyrimidin-3-yl)carbonyl)amino)-butanoate A mixture of (5R)-2,7,7-trimethyl-5-phenyl-4,5,6,7-tetrahydropyrazolo[1,5-a]pyrimidine-3-carboxylic acid (516 mg), HATU (825 mg), DIPEA (280 mg) and DMA (5 mL) was stirred at room temperature for 5 minutes. Then, a mixture of methyl 2-amino-2-(4-ethylphenyl)butanoate (400 mg) and DMA (2 mL) was added and the obtained mixture was stirred at 80° C. for 2 days. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate) to yield the title compound (178 mg).

MS: $[M+H]^+$ 489.2.

B) 2-(4-Ethylphenyl)-2-(((((5R)-2,7,7-trimethyl-5-phenyl-4,5,6,7-tetrahydropyrazolo[1,5-a]pyrimidin-3-yl)carbonyl)amino)butanoic acid A mixture of methyl 2-(4-ethylphenyl)-2-(((((5R)-2,7,7-trimethyl-5-phenyl-4,5,6,7-tetrahydropyrazolo[1,5-a]pyrimidin-3-yl)carbonyl)amino)butanoate (178 mg), THF (2 mL), methanol (2 mL) and 8 M aqueous solution of sodium hydroxide (2 mL) was stirred at 75° C. for 1 hour. The mixture was acidified with 6 M hydrochloric acid at 0° C., and extracted with ethyl acetate. The organic layer was separated, washed with saturated brine, then dried over anhydrous magnesium sulfate, and then concentrated under reduced pressure to yield the title compound (191 mg).

MS: 475.3.

C) (5R)—N-((2S)-1-(((2S)-1-Amino-1-oxopropan-2-yl)amino)-2-(4-ethylphenyl)-1-oxobutan-2-yl)-2,7,7-trimethyl-5-phenyl-4,5,6,7-tetrahydropyrazolo[1,5-a]pyrimidine-3-carboxamide A mixture of 2-(4-ethylphenyl)-2-(((((5R)-2,7,7-trimethyl-5-phenyl-4,5,6,7-tetrahydropyrazolo[1,5-a]pyrimidin-3-yl)carbonyl)amino)butanoic acid (191 mg), L-alaninamide hydrochloride (60.2 mg), HATU (184 mg), DIPEA (156 mg) and DMF (2 mL) was stirred at room temperature overnight, then stirred at 70° C. overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate), and the obtained fraction was concentrated under reduced pressure. The residue was fractionated by HPLC (CHIRALPAK IC (trade name), 50 mmID× 500 mmL), mobile phase: hexane/2-propanol=500/500 (v/v)), and the one having longer retention time was taken as the title compound (31.9 mg).

Optical purity: 98.2% d.e.

One having longer retention time under the following optical analysis condition

Column: CHIRALPAK IC (trade name) 4.6 mmID×250 mmL

Mobile phase: hexane/2-propanol=500/500 (v/v)

$^1$H NMR (300 MHz, DMSO-d$_6$) δ 0.72 (3H, t, J=7.3 Hz), 1.10-1.20 (6H, m), 1.44 (3H, s), 1.48 (3H, s), 1.94-2.14 (2H, m), 2.39-2.60 (6H, m), 2.62-2.76 (1H, m), 4.20 (1H, quin, J=7.1 Hz), 4.59 (1H, dd, J=11.0, 3.1 Hz), 6.35 (1H, s), 6.95 (2H, d, J=7.7 Hz), 7.14 (2H, d, J=8.3 Hz), 7.24-7.45 (7H, m), 7.49 (1H, s), 7.61 (1H, d, J=7.4 Hz).

Example 4

(5R)—N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

(5R)—N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (217 mg) was fractionated by HPLC(CHIRALPAK IA (trade name), 50 mmID×500 mmL), mobile phase: hexane/ethanol=650/350 (v/v)), and the one having longer retention time was taken as the title compound (90.1 mg).

Optical purity: 99.9% d.e.

One having longer retention time under the following optical analysis condition

Column: CHIRALPAK IA (trade name) 4.6 mmID×250 mmL

Mobile phase: hexane/ethanol=650/350 (v/v)

$^1$H NMR (300 MHz, DMSO-$d_6$) δ 0.74 (3H, t, J=7.3 Hz), 1.05-1.22 (6H, m), 1.48 (3H, s), 1.49 (3H, s), 2.00-2.20 (2H, m), 2.32-2.62 (4H, m), 4.07-4.19 (1H, m), 4.65 (1H, dd, J=11.2, 3.0 Hz), 6.26 (1H, s), 6.95 (1H, s), 7.13 (2H, d, J=8.4 Hz), 7.20 (1H, s), 7.27-7.44 (7H, m), 7.64 (1H, d, J=7.4 Hz), 7.74 (1H, s), 7.85 (1H, s).

Example 5

(5R)—N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

(5R)—N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (217 mg) was fractionated by HPLC(CHIRALPAK IA (trade name), 50 mmID×500 mmL), mobile phase: hexane/ethanol=650/350 (v/v)), and the one having shorter retention time was taken as the title compound (69.2 mg).

Optical purity: >99.9% d.e.

One having shorter retention time under the following optical analysis condition Column: CHIRALPAK IA (trade name) 4.6 mmID×250 mmL Mobile phase: hexane/ethanol=650/350 (v/v)

$^1$H NMR (300 MHz, DMSO-$d_6$) δ 0.69 (3H, t, J=7.3 Hz), 1.08-1.22 (6H, m), 1.48 (3H, s), 1.49 (3H, s), 1.97-2.20 (2H, m), 2.31-2.52 (2H, m), 2.58 (2H, q, J=7.6 Hz), 4.02-4.13 (1H, m), 4.66 (1H, dd, J=11.1, 2.9 Hz), 6.33 (1H, s), 6.94 (1H, s), 7.18 (3H, d, J=8.2 Hz), 7.26-7.48 (7H, m), 7.68-7.84 (2H, m), 7.93 (1H, s).

Example 6

(5R)—N-(1-(((2S)-1-Amino-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

A mixture of 2-((((5R)-7,7-dimethyl-5-phenyl-4,5,6,7-tetrahydropyrazolo[1,5-a]pyrimidin-3-yl)carbonyl)amino)-2-(4-ethylphenyl)butanoic acid (150 mg), (2S)-2-aminobutanamide hydrochloride (54.2 mg), HATU (149 mg), DIPEA (126 mg) and DMF (1 ml) was stirred at room temperature overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate, then ethyl acetate/methanol), and the obtained fraction was concentrated under reduced pressure. The residue was fractionated by SFC(CHIRALPAK IC (trade name), 20 mmID×250 mmL), mobile phase: carbon dioxide/ethanol=600/400 (v/v)), and the one having shorter retention time was taken as the title compound (48.4 mg).

Optical purity: >99% d.e.

One having shorter retention time under the following optical analysis condition Column: CHIRALPAK IC (trade name) 4.6 mmID×150 mmL Mobile phase: carbon dioxide/ethanol=600/400 (v/v)

$^1$H NMR (300 MHz, DMSO-$d_6$) δ 0.54 (3H, t, J=7.4 Hz), 0.72 (3H, t, J=7.3 Hz), 1.11-1.19 (3H, m), 1.37-1.54 (7H, m), 1.55-1.75 (1H, m), 2.01-2.19 (2H, m), 2.37-2.48 (2H, m), 2.56 (2H, d, J=7.6 Hz), 3.98-4.07 (1H, m), 4.64 (1H, dd, J=11.1, 3.0 Hz), 6.25 (1H, s), 6.97 (1H, s), 7.13 (2H, d, J=8.3 Hz), 7.21 (1H, s), 7.26-7.47 (7H, m), 7.53 (1H, d, J=7.9 Hz), 7.76 (1H, s), 7.83 (1H, s).

Example 7

(5R)—N-(1-(((2S)-1-Amino-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

A mixture of 2-((((5R)-7,7-dimethyl-5-phenyl-4,5,6,7-tetrahydropyrazolo[1,5-a]pyrimidin-3-yl)carbonyl)amino)-2-(4-ethylphenyl)butanoic acid (150 mg), (2S)-2-aminobutanamide hydrochloride (54.2 mg), HATU (149 mg), DIPEA (126 mg) and DMF (1 ml) was stirred at room temperature overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate, then ethyl acetate/methanol), and the obtained fraction was concentrated under reduced pressure. The residue was fractionated by SFC(CHIRALPAK IC (trade name), 20 mmID×250 mmL), mobile phase: carbon dioxide/ethanol=600/400 (v/v)), and the one having longer retention time was taken as the title compound (46.8 mg).

Optical purity: >99% d.e.

One having longer retention time under the following optical analysis condition

Column: CHIRALPAK IC (trade name) 4.6 mmID×150 mmL

Mobile phase: carbon dioxide/ethanol=600/400 (v/v)

$^1$H NMR (300 MHz, DMSO-$d_6$) δ 0.56 (3H, t, J=7.4 Hz), 0.70 (3H, t, J=7.3 Hz), 1.12-1.19 (3H, m), 1.38-1.59 (7H, m), 1.65-1.83 (1H, m), 1.95-2.20 (2H, m), 2.32-2.44 (1H, m), 2.51-2.65 (3H, m), 3.88-3.99 (1H, m), 4.66 (1H, dd, J=11.1, 2.7 Hz), 6.33 (1H, s), 6.93 (1H, s), 7.17 (3H, d, J=8.4 Hz), 7.28-7.49 (7H, m), 7.64 (1H, d, J=7.8 Hz), 7.77 (1H, s), 7.95 (1H, s).

Example 8

(5R)—N-(1-(((2S)-1-Amino-4-methyl-1-oxopentan-2-yl)amino)-2-(4-ethylphenyl)-1-oxopropan-2-yl)-7,7-dimethyl-5-phenyl-4,5,6,7-tetrahydropyrazolo[1,5-a]pyrimidine-3-carboxamide (optical isomer)

A) Methyl 2-((((5R)-7,7-dimethyl-5-phenyl-4,5,6,7-tetrahydropyrazolo[1,5-a]pyrimidin-3-yl)carbonyl)amino)-2-(4-ethylphenyl)propanoate A mixture of (5R)-7,7-dimethyl-5-phenyl-4,5,6,7-tetrahydropyrazolo[1,5-a]pyrimidine-3-carboxylic acid (321 mg), HATU (539 mg), DIPEA (183 mg) and DMA (3 ml) was stirred at room temperature for 5 minutes. Then, a mixture of methyl 2-amino-2-(4-ethylphenyl)propanoate (490 mg) and DMA (3 ml) was added and the mixture was stirred at 80° C. overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate) to yield the title compound (385 mg)

MS: [M+H]$^+$ 461.2.

B) 2-((((5R)-7,7-Dimethyl-5-phenyl-4,5,6,7-tetrahydropyrazolo[1,5-a]pyrimidin-3-yl)carbonyl)amino)-2-(4-ethylphenyl)propanoic acid A mixture of methyl 2-((((5R)-7,7-dimethyl-5-phenyl-4,5,6,7-tetrahydropyrazolo[1,5-a]pyrimidin-3-yl)carbonyl)amino)-2-(4-ethylphenyl)propanoate (370 mg), THF (3 ml), methanol (3 mL) and 8 M aqueous solution of sodium hydroxide (3 mL) was stirred at 75° C. for 1 hour. The mixture was acidified with 6 M hydrochloric acid at 0° C., and extracted with ethyl acetate. The organic layer was separated, washed with saturated brine, then dried over anhydrous magnesium sulfate, and then concentrated under reduced pressure to yield the title compound (357 mg).

MS: 447.2.

C) (5R)—N-(1-(((2S)-1-Amino-4-methyl-1-oxopentan-2-yl)amino)-2-(4-ethylphenyl)-1-oxopropan-2-yl)-7,7-dimethyl-5-phenyl-4,5,6,7-tetrahydropyrazolo[1,5-a]pyrimidine-3-carboxamide (optical isomer)

A mixture of 2-((((5R)-7,7-dimethyl-5-phenyl-4,5,6,7-tetrahydropyrazolo[1,5-a]pyrimidin-3-yl)carbonyl)amino)-2-(4-ethylphenyl)propanoic acid (345 mg), L-leucinamide (121 mg), HATU (353 mg), DIPEA (120 mg) and DMF (4 ml) was stirred at 70° C. for 6 hours. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate), and the obtained fraction was concentrated under reduced pressure. The residue was fractionated by HPLC (CHIRALPAK ID (trade name), 50 mmID× 500 mmL), mobile phase: hexane/ethanol=400/600 (v/v)), and the one having shorter retention time was taken as the title compound (63.7 mg).

Optical purity: >99.9% d.e.

One having shorter retention time under the following optical analysis condition Column: CHIRALPAK ID (trade name) 4.6 mmID×250 mmL Mobile phase: hexane/ethanol=400/600 (v/v)

$^1$H NMR (300 MHz, DMSO-d$_6$) δ 0.49 (3H, d, J=6.5 Hz), 0.70 (3H, d, J=6.6 Hz), 1.12-1.24 (5H, m), 1.49 (7H, d, J=1.9 Hz), 1.76 (3H, s), 1.92-2.06 (1H, m), 2.18 (1H, d, J=13.0 Hz), 2.58 (2H, q, J=7.6 Hz), 3.96-4.05 (1H, m), 4.68 (1H, d, J=8.8 Hz), 6.40 (1H, s), 6.91 (1H, brs), 7.13-7.48 (10H, m), 7.78-7.88 (1H, m), 7.91-8.03 (2H, m).

Example 9

(5R)—N-(1-(((2S)-1-Amino-4-methyl-1-oxopentan-2-yl)amino)-2-(4-ethylphenyl)-1-oxopropan-2-yl)-7,7-dimethyl-5-phenyl-4,5,6,7-tetrahydropyrazolo[1,5-a]pyrimidine-3-carboxamide (optical isomer)

A mixture of 2-((((5R)-7,7-dimethyl-5-phenyl-4,5,6,7-tetrahydropyrazolo[1,5-a]pyrimidin-3-yl)carbonyl)amino)-2-(4-ethylphenyl)propanoic acid (345 mg), L-leucinamide (121 mg), HATU (353 mg), DIPEA (120 mg) and DMF (4 ml) was stirred at 70° C. for 6 hours. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate), and the obtained fraction was concentrated under reduced pressure. The residue was fractionated by HPLC (CHIRALPAK ID (trade name), 50 mmID× 500 mmL), mobile phase: hexane/ethanol=400/600 (v/v)), and the one having longer retention time was taken as the title compound (44.9 mg).

Optical purity: 99.9% d.e.

One having longer retention time under the following optical analysis condition

Column: CHIRALPAK ID (trade name) 4.6 mmID×250 mmL

Mobile phase: hexane/ethanol=400/600 (v/v)

$^1$H NMR (300 MHz, DMSO-d$_6$) δ 0.69 (6H, t, J=6.8 Hz), 1.10-1.26 (5H, m), 1.41-1.54 (7H, m), 1.75 (3H, s), 1.95-2.06 (1H, m), 2.12-2.21 (1H, m), 2.56 (2H, q, J=7.7 Hz), 4.02-4.13 (1H, m), 4.64 (1H, dd, J=11.2, 2.7 Hz), 6.32 (1H, s), 6.88 (1H, s), 7.06-7.18 (3H, m), 7.27-7.46 (7H, m), 7.81 (1H, d, J=8.0 Hz), 7.88 (1H, s), 7.95 (1H, s).

Example 10

(5R)—N-(1-(((2S,3S)-1-Amino-3-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

A mixture of 2-((((5R)-7,7-dimethyl-5-phenyl-4,5,6,7-tetrahydropyrazolo[1,5-a]pyrimidin-3-yl)carbonyl)amino)-2-(4-ethylphenyl)butanoic acid (150 mg), L-isoleucinamide hydrochloride (65.1 mg), HATU (149 mg), DIPEA (126 mg) and DMF (1 ml) was stirred at room temperature overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate, then ethyl acetate/methanol), and the obtained fraction was concentrated under reduced pressure. The residue was fractionated by SFC(CHIRALPAK IC (trade name), 20 mmID×250 mmL), mobile phase: carbon dioxide/ethanol=600/400 (v/v)), and the one having shorter retention time was taken as the title compound (50.9 mg).

Optical purity: >99% d.e.

One having shorter retention time under the following optical analysis condition Column: CHIRALPAK IC (trade name) 4.6 mmID×150 mmL Mobile phase: carbon dioxide/ethanol=600/400 (v/v)

$^1$H NMR (300 MHz, DMSO-d$_6$) δ 0.52-0.62 (3H, m), 0.63-0.78 (7H, m), 1.01-1.19 (4H, m), 1.47 (3H, s), 1.51 (3H, s), 1.54-1.65 (1H, m), 2.00-2.22 (2H, m), 2.44 (2H, q, J=7.1 Hz), 2.56 (2H, q, J=7.6 Hz), 3.97-4.07 (1H, m), 4.63 (1H, dd, J=11.1, 3.0 Hz), 6.27 (1H, s), 6.99 (1H, s), 7.13 (2H, d, J=8.3 Hz), 7.22-7.45 (9H, m), 7.75 (1H, s), 7.81 (1H, s).

Example 11

(5R)—N-(1-(((2S,3S)-1-Amino-3-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

A mixture of 2-((((5R)-7,7-dimethyl-5-phenyl-4,5,6,7-tetrahydropyrazolo[1,5-a]pyrimidin-3-yl)carbonyl)amino)-2-(4-ethylphenyl)butanoic acid (150 mg), L-isoleucinamide hydrochloride (65.1 mg), HATU (149 mg), DIPEA (126 mg) and DMF (1 ml) was stirred at room temperature overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate, then ethyl acetate/methanol), and the obtained fraction was concentrated under reduced pressure. The residue was fractionated by SFC(CHIRALPAK IC (trade name), 20 mmID×250 mmL), mobile phase: carbon dioxide/ethanol=600/400 (v/v)), and the one having longer retention time was taken as the title compound (45.0 mg).

Optical purity: >99% d.e.

One having longer retention time under the following optical analysis condition

Column: CHIRALPAK IC (trade name) 4.6 mmID×150 mmL

Mobile phase: carbon dioxide/ethanol=600/400 (v/v)

$^1$H NMR (300 MHz, DMSO-d$_6$) δ 0.63-0.77 (9H, m), 0.86-1.01 (1H, m), 1.12-1.19 (3H, m), 1.22-1.35 (1H, m), 1.47 (3H, s), 1.50 (3H, s), 1.63-1.80 (1H, m), 2.02-2.19 (2H, m), 2.35 (1H, dq, J=14.2, 7.1 Hz), 2.45-2.64 (3H, m), 3.98-4.10 (1H, m), 4.63 (1H, dd, J=11.0, 3.1 Hz), 6.28 (1H, s), 6.95 (1H, s), 7.14 (2H, d, J=8.4 Hz), 7.20-7.47 (9H, m), 7.77 (1H, s), 7.88 (1H, s).

Example 12

(5R)—N-(1-(((2S)-1-Amino-3-methyl-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

A mixture of 2-((((5R)-7,7-dimethyl-5-phenyl-4,5,6,7-tetrahydropyrazolo[1,5-a]pyrimidin-3-yl)carbonyl)amino)-2-(4-ethylphenyl)butanoic acid (150 mg), L-valinamide hydrochloride (59.6 mg), HATU (149 mg), DIPEA (126 mg) and DMF (1 ml) was stirred at room temperature overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate, then ethyl acetate/methanol), and the obtained fraction was concentrated under reduced pressure. The residue was fractionated by SFC(CHIRALPAK IC (trade name), 20 mmID×250 mmL), mobile phase: carbon dioxide/ethanol=660/340 (v/v)), and the one having shorter retention time was taken as the title compound (53.5 mg).

Optical purity: 99% d.e.

One having shorter retention time under the following optical analysis condition Column: CHIRALPAK IC (trade name) 4.6 mmID×150 mmL Mobile phase: carbon dioxide/ethanol=660/340 (v/v)

$^1$H NMR (300 MHz, DMSO-d$_6$) δ 0.53 (3H, d, J=6.8 Hz), 0.63-0.76 (6H, m), 1.11-1.19 (3H, m), 1.47 (3H, s), 1.50 (3H, s), 1.86 (1H, dq, J=13.4, 6.8 Hz), 1.98-2.17 (2H, m), 2.35-2.47 (2H, m), 2.56 (2H, q, J=7.7 Hz), 4.01-4.09 (1H, m), 4.64 (1H, dd, J=11.2, 3.0 Hz), 6.27 (1H, s), 7.02 (1H, s), 7.13 (2H, d, J=8.3 Hz), 7.26-7.44 (9H, m), 7.75 (1H, s), 7.81 (1H, s).

Example 13

(5R)—N-(1-(((2S)-1-Amino-3-methyl-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

A mixture of 2-((((5R)-7,7-dimethyl-5-phenyl-4,5,6,7-tetrahydropyrazolo[1,5-a]pyrimidin-3-yl)carbonyl)amino)-2-(4-ethylphenyl)butanoic acid (150 mg), L-valinamide hydrochloride (59.6 mg), HATU (149 mg), DIPEA (126 mg) and DMF (1 ml) was stirred at room temperature overnight. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate, then ethyl acetate/methanol), and the obtained fraction was concentrated under reduced pressure. The residue was fractionated by SFC(CHIRALPAK IC (trade name), 20 mmID×250 mmL), mobile phase: carbon dioxide/ethanol=660/340 (v/v)), and the one having longer retention time was taken as the title compound (50.1 mg).

Optical purity: 99% d.e.

One having longer retention time under the following optical analysis condition

Column: CHIRALPAK IC (trade name) 4.6 mmID×150 mmL

Mobile phase: carbon dioxide/ethanol=660/340 (v/v)

$^1$H NMR (300 MHz, DMSO-d$_6$) δ 0.59-0.78 (9H, m), 1.11-1.19 (3H, m), 1.47 (3H, s), 1.50 (3H, s), 1.91-2.19 (3H, m), 2.27-2.45 (1H, m), 2.45-2.66 (3H, m), 3.98-4.08 (1H, m), 4.64 (1H, dd, J=11.0, 3.2 Hz), 6.28 (1H, s), 6.97 (1H, s), 7.15 (2H, d, J=8.3 Hz), 7.20-7.48 (9H, m), 7.77 (1H, s), 7.88 (1H, s).

Example 15

(5R)—N-(1-(((2S)-1-Amino-4-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

(5R)—N-(1-(((2S)-1-Amino-4-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (98.5 mg) was fractionated by HPLC (CHIRALPAK IC (trade name), 50 mmID×500 mmL), mobile phase: hexane/ethanol=600/400 (v/v)), and the one having shorter retention time was taken as the title compound (18.3 mg).

Optical purity: >99.9% d.e.

One having shorter retention time under the following optical analysis condition Column: CHIRALPAK IC (trade name) 4.6 mmID×250 mmL Mobile phase: hexane/ethanol=600/400 (v/v)

$^1$H NMR (300 MHz, DMSO-$d_6$) δ 0.59 (3H, d, J=6.4 Hz), 0.64 (3H, d, J=6.6 Hz), 0.72 (3H, t, J=7.3 Hz), 1.11-1.18 (3H, m), 1.21-1.46 (3H, m), 1.48 (3H, s), 1.50 (3H, s), 2.00-2.19 (2H, m), 2.40-2.61 (4H, m), 4.03-4.19 (1H, m), 4.63 (1H, dd, J=11.4, 2.8 Hz), 6.25 (1H, s), 6.89 (1H, s), 7.07 (1H, s), 7.12 (2H, d, J=8.3 Hz), 7.28-7.46 (7H, m), 7.60 (1H, d, J=8.1 Hz), 7.77 (1H, s), 7.84 (1H, s).

Example 16

(5R)—N-(1-(((2S)-1-Amino-4-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

(5R)—N-(1-(((2S)-1-Amino-4-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (98.5 mg) was fractionated by HPLC (CHIRALPAK IC (trade name), 50 mmID×500 mmL), mobile phase: hexane/ethanol=600/400 (v/v)), and the one having longer retention time was taken as the title compound (17.9 mg).

Optical purity: 99.4% d.e.

One having longer retention time under the following optical analysis condition

Column: CHIRALPAK IC (trade name) 4.6 mmID×250 mmL

Mobile phase: hexane/ethanol=600/400 (v/v)

$^1$H NMR (300 MHz, DMSO-$d_6$) δ 0.46 (3H, d, J=6.5 Hz), 0.65-0.74 (6H, m), 1.03-1.25 (4H, m), 1.33-1.54 (8H, m), 1.92-2.20 (2H, m), 2.29-2.41 (1H, m), 2.52-2.63 (3H, m), 3.91-4.13 (1H, m), 4.67 (1H, dd, J=11.2, 2.6 Hz), 6.35 (1H, s), 6.88 (1H, brs), 7.07 (1H, brs), 7.16 (2H, d, J=8.3 Hz), 7.26-7.47 (7H, m), 7.74 (1H, d, J=8.4 Hz), 7.83 (1H, s), 8.01 (1H, s).

Example 27

(5R)—N-(1-Amino-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

(5R)—N-(1-Amino-2-(4-ethylphenyl)-1-oxobutan-2-yl)-7,7-dimethyl-5-phenyl-4,5,6,7-tetrahydropyrazolo[1,5-a]pyrimidine-3-carboxamide (20.6 mg) was fractionated by SFC(CHIRALPAK ASH (trade name), 20 mmID×250 mmL), mobile phase: carbon dioxide/methanol=820/180 (v/v)), and the one having shorter retention time was taken as the title compound (9.1 mg).

Optical purity: >99% d.e.

One having shorter retention time under the following optical analysis condition Column: CHIRALPAK ASH (trade name) 4.6 mmID× 150 mmL Mobile phase: carbon dioxide/methanol=820/180 (v/v).

Example 28

(5R)—N-(1-Amino-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

(5R)—N-(1-Amino-2-(4-ethylphenyl)-1-oxobutan-2-yl)-7,7-dimethyl-5-phenyl-4,5,6,7-tetrahydropyrazolo[1,5-a]pyrimidine-3-carboxamide (20.6 mg) was fractionated by SFC(CHIRALPAK ASH (trade name), 20 mmID×250 mmL), mobile phase: carbon dioxide/methanol=820/180 (v/v)), and the one having longer retention time was taken as the title compound (7.0 mg).

Optical purity: 98% d.e.

One having longer retention time under the following optical analysis condition

Column: CHIRALPAK ASH (trade name) 4.6 mmID× 150 mmL

Mobile phase: carbon dioxide/methanol=820/180 (v/v)

Example 30

(5R)—N-(2-(4-Ethylphenyl)-1-(methylamino)-1-oxobutan-2-yl)-7,7-dimethyl-5-phenyl-4,5,6,7-tetrahydropyrazolo[1,5-a]pyrimidine-3-carboxamide (optical isomer)

(5R)—N-(2-(4-Ethylphenyl)-1-(methylamino)-1-oxobutan-2-yl)-7,7-dimethyl-5-phenyl-4,5,6,7-tetrahydropyrazolo[1,5-a]pyrimidine-3-carboxamide (81.2 mg) was fractionated by SFC(CHIRALPAK ASH (trade name), 20 mmID× 250 mmL), mobile phase: carbon dioxide/ethanol=900/100 (v/v)), and the one having shorter retention time was taken as the title compound (30.1 mg).

Optical purity: >99% d.e.

One having shorter retention time under the following optical analysis condition Column: CHIRALPAK ASH (trade name) 4.6 mmID× 150 mmL Mobile phase: carbon dioxide/ethanol=900/100 (v/v)

Example 31

(5R)—N-(2-(4-Ethylphenyl)-1-(methylamino)-1-oxobutan-2-yl)-7,7-dimethyl-5-phenyl-4,5,6,7-tetrahydropyrazolo[1,5-a]pyrimidine-3-carboxamide (optical isomer)

(5R)—N-(2-(4-Ethylphenyl)-1-(methylamino)-1-oxobutan-2-yl)-7,7-dimethyl-5-phenyl-4,5,6,7-tetrahydropyrazolo[1,5-a]pyrimidine-3-carboxamide (81.2 mg) was fractionated by SFC(CHIRALPAK ASH (trade name), 20 mmID× 250 mmL), mobile phase: carbon dioxide/ethanol=900/100 (v/v)), and the one having longer retention time was taken as the title compound (27.2 mg).

Optical purity: >99% d.e.

One having longer retention time under the following optical analysis condition

Column: CHIRALPAK ASH (trade name) 4.6 mmID× 150 mmL

Mobile phase: carbon dioxide/ethanol=900/100 (v/v)

Example 32

(5R)—N-(1-(Dimethylamino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

A mixture of 2-((((5R)-7,7-dimethyl-5-phenyl-4,5,6,7-tetrahydropyrazolo[1,5-a]pyrimidin-3-yl)carbonyl)amino)-2-(4-ethylphenyl)butanoic acid (100 mg), N-methyl methanamine hydrochloride (53.1 mg), HATU (99 mg), DIPEA (126 mg) and DMF (1 ml) was stirred at 70° C. for 4 hours. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate), and the fraction having lower polarity was concentrated under reduced pressure to yield the title compound (40.0 mg).

$^1$H NMR (400 MHz, DMSO-$d_6$) δ 0.68 (3H, t, J=7.3 Hz), 1.14-1.18 (3H, m), 1.44 (3H, s), 1.51 (3H, s), 2.02-2.16 (2H, m), 2.21-2.39 (1H, m), 2.51-3.09 (9H, m), 4.60 (1H, dd, J=10.3, 4.2 Hz), 6.24 (1H, s), 7.17 (2H, d, J=8.3 Hz), 7.25-7.49 (7H, m), 7.73 (1H, s), 7.87 (1H, s).

Example 33

(5R)—N-(1-(Dimethylamino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer)

A mixture of 2-((((5R)-7,7-dimethyl-5-phenyl-4,5,6,7-tetrahydropyrazolo[1,5-a]pyrimidin-3-yl)carbonyl)amino)-2-(4-ethylphenyl)butanoic acid (100 mg), N-methyl methanamine hydrochloride (53.1 mg), HATU (99 mg), DIPEA (126 mg) and DMF (1 ml) was stirred at 70° C. for 4 hours. Water was added to the mixture, and the obtained mixture was extracted with ethyl acetate. The organic layer was separated, washed with saturated brine, then dried over anhydrous magnesium sulfate, and then concentrated under reduced pressure. The residue was purified by silica gel column chromatography (hexane/ethyl acetate), and the fraction having higher polarity was concentrated under reduced pressure to yield the title compound (39.6 mg).

$^1$H NMR (400 MHz, DMSO-$d_6$) δ 0.66 (3H, t, J=7.3 Hz), 1.15-1.21 (3H, m), 1.47 (3H, s), 1.49 (3H, s), 2.02-2.17 (2H, m), 2.33 (1H, dq, J=14.1, 7.2 Hz), 2.53-2.95 (9H, m), 4.65 (1H, dd, J=11.4, 2.9 Hz), 6.25 (1H, s), 7.19 (2H, d, J=8.3 Hz), 7.26-7.50 (7H, m), 7.77 (1H, s), 7.83 (1H, s).

The compounds of Examples are shown in the following tables. MS in the Table means the measured values. According to the method shown in the above Examples or the method conforming to those, the compounds of Examples 14, 17-26, 29 shown in the following Tables were produced.

TABLE 7

| Example No. | IUPAC name | Structural formula | Salt | MS |
|---|---|---|---|---|
| 1 | (5R)-N-((2R)-1-(((2S)-1-Amino-1-oxopropan-2-yl)amino)-2-(4-ethylphenyl)-1-oxobutan-2-yl)-2,7,7-trimethyl-5-phenyl-4,5,6,7-tetrahydropyrazolo[1,5-a]pyrimidine-3-carboxamide | | | 545.3 |
| 2 | (5R)-N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide | | | 531.4 |

TABLE 7-continued

| Example No. | IUPAC name | Structural formula | Salt | MS |
|---|---|---|---|---|
| 3 | (5R)-N-((2S)-1-(((2S)-1-Amino-1-oxopropan-2-yl)amino)-2-(4-ethylphenyl)-1-oxobutan-2-yl)-2,7,7-trimethyl-5-phenyl-4,5,6,7-tetrahydropyrazolo[1,5-a]pyrimidine-3-carboxamide | | | 545.3 |
| 4 | (5R)-N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 531.3 |
| 5 | (5R)-N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 531.3 |
| 6 | (5R)-N-(1-(((2S)-1-Amino-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 545.4 |

TABLE 7-continued

| Example No. | IUPAC name | Structural formula | Salt | MS |
|---|---|---|---|---|
| 7 | (5R)-N-(1-(((2S)-1-Amino-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 545.4 |
| 8 | (5R)-N-(1-(((2S)-1-Amino-4-methyl-1-oxopentan-2-yl)amino)-2-(4-ethylphenyl)-1-oxopropan-2-yl)-7,7-dimethyl-5-phenyl-4,5,6,7-tetrahydropyrazolo[1,5-a]pyrimidine-3-carboxamide (optical isomer) | | | 559.4 |
| 9 | (5R)-N-(1-(((2S)-1-Amino-4-methyl-1-oxopentan-2-yl)amino)-2-(4-ethylphenyl)-1-oxopropan-2-yl)-7,7-dimethyl-5-phenyl-4,5,6,7-tetrahydropyrazolo[1,5-a]pyrimidine-3-carboxamide (optical isomer) | | | 559.4 |
| 10 | (5R)-N-(1-(((2S,3S)-1-Amino-3-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 573.5 |

TABLE 7-continued

| Example No. | IUPAC name | Structural formula | Salt | MS |
|---|---|---|---|---|
| 11 | (5R)-N-(1-(((2S,3S)-1-Amino-3-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 573.5 |
| 12 | (5R)-N-(1-(((2S)-1-Amino-3-methyl-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 559.4 |
| 13 | (5R)-N-(1-(((2S)-1-Amino-3-methyl-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 559.4 |
| 14 | (5R)-N-(1-(((2S)-1-Amino-4-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide | | | 573.5 |

TABLE 7-continued

| Example No. | IUPAC name | Structural formula | Salt | MS |
|---|---|---|---|---|
| 15 | (5R)-N-(1-(((2S)-1-Amino-4-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide | | | 573.5 |
| 16 | (5R)-N-(1-(((2S)-1-Amino-4-methyl-1-oxopentan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 573.5 |
| 17 | (5R)-N-(1-((2-Amino-2-oxoethyl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide | | | 517.4 |
| 18 | Alpha-(2-((((5R)-7,7-dimethyl-5-phenyl-4,5,6,7-tetrahydropyrazolo[1,5-a]pyrimidin-3-yl)carbonyl)amino)-2-(4-ethylphenyl)butanoyl-L-phenylalaninamide | | | 607.4 |

TABLE 7-continued

| Example No. | IUPAC name | Structural formula | Salt | MS |
|---|---|---|---|---|
| 19 | N²-(2-((((5R)-7,7-Dimethyl-5-phenyl-4,5,6,7-tetrahydropyrazolo[1,5-a]pyrimidin-3-yl)carbonyl)amino)-2-(4-ethylphenyl)butanoyl-L-alpha-asparagine | | | 575.4 |
| 20 | (5R)-N-(1-(((2S)-1,6-Diamino-1-oxohexan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide | | | 588.6 |
| 21 | (5R)-N-((2R)-1-(((2S,3R)-1-Amino-3-hydroxy-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide | | | 561.4 |
| 22 | (5R)-N-(1-(((2R)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide | | | 531.4 |

TABLE 7-continued

| Example No. | IUPAC name | Structural formula | Salt | MS |
|---|---|---|---|---|
| 23 | (5R)-N-(1-(((2S)-1-Amino-3-hydroxy-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide | | | 547.4 |
| 24 | N²-(2-((((5R)-7,7-Dimethyl-5-phenyl-4,5,6,7-tetrahydropyrazolo[1,5-a]pyrimidin-3-yl)carbonyl)amino)-2-(4-ethylphenyl)butanoyl-L-aspartamide | | | 574.5 |
| 25 | N-(2-((((5R)-7,7-Dimethyl-5-phenyl-4,5,6,7-tetrahydropyrazolo[1,5-a]pyrimidin-3-yl)carbonyl)amino)-2-(4-ethylphenyl)butanoyl-glycine | | | 518.4 |
| 26 | (5R)-N-(1-Amino-2-(4-ethylphenyl)-1-oxobutan-2-yl)-7,7-dimethyl-5-phenyl-4,5,6,7-tetrahydropyrazolo[1,5-a]pyrimidine-3-carboxamide | | | 460.4 |

TABLE 7-continued

| Example No. | IUPAC name | Structural formula | Salt | MS |
|---|---|---|---|---|
| 27 | (5R)-N-(1-Amino-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 460.3 |
| 28 | (5R)-N-(1-Amino-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 460.3 |
| 29 | (5R)-N-(2-(4-Ethylphenyl)-1-(methylamino)-1-oxobutan-2-yl)-7,7-dimethyl-5-phenyl-4,5,6,7-tetrahydropyrazolo[1,5-a]pyrimidine-3-carboxamide | | | 474.3 |
| 30 | (5R)-N-(2-(4-Ethylphenyl)-1-(methylamino)-1-oxobutan-2-yl)-7,7-dimethyl-5-phenyl-4,5,6,7-tetrahydropyrazolo[1,5-a]pyrimidine-3-carboxamide (optical isomer) | | | 474.3 |
| 31 | (5R)-N-(2-(4-Ethylphenyl)-1-(methylamino)-1-oxobutan-2-yl)-7,7-dimethyl-5-phenyl-4,5,6,7-tetrahydropyrazolo[1,5-a]pyrimidine-3-carboxamide (optical isomer) | | | 474.3 |

TABLE 7-continued

| Example No. | IUPAC name | Structural formula | Salt | MS |
|---|---|---|---|---|
| 32 | (5R)-N-(1-(Dimethylamino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 488.3 |
| 33 | (5R)-N-(1-(Dimethylamino)-2-(4-ethylphenyl)-1-oxobutan-2-yl)-7,7-dimethyl-5-phenyl-4,5,6,7-tetrahydropyrazolo[1,5-a]pyrimidine-3-carboxamide (optical isomer) | | | 488.3 |

[Test Example 1] CYP Induction

Cryopreserved hepatocytes were thawed in a culture medium (In VitroGRO™ CP Medium, Celsis In Vitro Technologies, U.S.A.), and the resultant was added to BioCoat™ Matrigel®™ Matrix Thin-Layer 96 well (Becton, Dickinson and Company, U.S.A.) at a concentration of 40,000 cells/well. After culturing for 24 hours, the culture medium was removed, and replaced with an incubation medium (In VitroGRO™, HI Medium with Torpedo Antibiotic Mix, Celsis In Vitro Technologies, U.S.A.). Cells were cultured for an additional 3 days. The medium was removed on day 4, and the remained cells were treated in the induction medium containing a test compound for 3 days in the presence or absence of 10 μmol/L rifampicin. The induction medium was replaced every day. The test compound addition wells in the presence of 10 μmol/L rifampicin were used to evaluate the inhibitory effect of the test compound on the inducibility of the CYP3A activity by rifampicin. The CYP3A activity was evaluated by measuring luciferin generating amount after the addition of 2 μmol/L luciferin-IPA using IPA P450-Glo™ CYP3A4 assay systems (Promega Corporation, U.S.A.). All cultures were carried out under a humidified environment at 37° C., 5% $CO_2$. The inducibility by rifampicin was defines as 100%, and the inducibility of the test compound (% of positive control) was calculated from the following equation:

[(luciferin fluorescence intensity in the absence of rifampicin and the presence of test compound)−(luciferin fluorescence intensity in the absence of rifampicin and test compound)/(luciferin fluorescence intensity in the presence of rifampicin and the absence of test compound)−(Luciferin fluorescence intensity in the absence of rifampicin and test compound)]×100.

The results are shown in Table 8.

TABLE 8

| Test compound (Example No.) | Inducibility (%) |
|---|---|
| 1 | 15.3 |
| 4 | 20.8 |
| 6 | 18.6 |
| 12 | 17.3 |

[Test Example 2] CYP3A4 TDI

Human liver microsomes purchased from XenoTech, LLC (Lenexa, KS) was used. Test compounds were dissolved in acetonitrile or DMSO/acetonitrile (1:4, v/v). To a human liver microsomes solution adjusted with phosphate buffer (pH 7.4), the test compound solution was added to obtain a human liver microsomes reaction solution having the test compound concentration of 30 μM. To the human liver microsome reaction solution, NADPH production system was added, and the mixture was preincubated at 37° C. for 0 minutes or 60 minutes. After the preincubation, probe substrate testosterone was added, and testosterone metabolite 6β-hydroxytestosterone was analyzed by LC/MS/MS to evaluate CYP3A4 enzymatic activity.

The enzyme activity (% of control) at each preincubation point was calculated from the following equation:

% of control={(activity of test compound addition group)/(activity of test compound non-addition group)}×100.

The remaining activity (% remaining) after 60 minutes of preincubation was calculated from the following equation:

Remaining activity (%)={activity after 60 minutes (% of control$_{60\ min}$)}/{activity after 0 minutes (% of control$_{0\ min}$)}×100.

The results are shown in Table 9.

TABLE 9

| Test compound (Example No.) | Remaining Activity (%) | Solvent |
| --- | --- | --- |
| 1 | 96.2 | DMSO/acetonitrile (1:4, v/v) |
| 4 | 95.6 | acetonitrile |
| 6 | 80.2 | acetonitrile |
| 12 | 74.3 | acetonitrile |

[Test Example 3] Human CaSR Antagonist Activity

CaSR antagonist activity measurement was performed using Bright-Glo Luciferase assay system (Promega Corporation). CHO cells in which human CaSR and NFAT-Luciferase reporter gene were forcibly expressed were suspended in MEM alpha (Wako Pure Chemical Industries, Ltd.) containing 10% dialyzed serum (HyClone). The cells in suspension was seeded in 384-well white plate (Corning) at 10,000/20 μL/well, and cultured in an incubator of 37° C., 5% $CO_2$ for one day. A diluent of Test compound was prepared with assay buffer (MEM alpha containing 10 mM HEPES (Life Technologies) and 10% dialysis serum). The diluent was added to the plate at 5 μL/well and allowed to stand at 37° C. for 10 minutes. Further, a diluent of 7.8 mM $CaCl_2$ prepared with assay buffer (final concentration 1.3 mM) was added at 5 μl/well and allowed to stand in an incubator of 37° C., 5% $CO_2$ for 2 hours. Bright-Glo reagents (Promega Corporation) were added at 10 μL/well, and the obtained mixture was stirred for 5 minutes, and then luminescence intensity was measured using Multi-label reader Envision (PerkinElmer, Inc.). The activity (%) of the test compound was calculated with the definitions in which the luminescence intensity when DMSO is added in place of the test compound is defined as 0% inhibition; and the luminescence intensity when (5R)—N-(1-ethyl-1-(4-ethylphenyl)propyl)-2,7,7-trimethyl-5-phenyl-4,5,6,7-tetrahydropyrazolo[1,5-a] Pyrimidine-3-carboxamide at final concentration of 10 μM is added is defined as 100% inhibition.

The results are shown in Table 10. As shown below, it has been found that compound (I) has an excellent CaSR antagonist activity.

TABLE 10

| Test compound (Example No.) | Inhibition rate (%) at 3.3 μM |
| --- | --- |
| 1 | 103 |
| 2 | 102 |
| 3 | 94 |
| 4 | 102 |
| 6 | 105 |
| 9 | 98 |

TABLE 10-continued

| Test compound (Example No.) | Inhibition rate (%) at 3.3 μM |
| --- | --- |
| 10 | 100 |
| 12 | 99 |
| 14 | 98 |
| 15 | 101 |
| 16 | 105 |
| 17 | 104 |
| 18 | 101 |
| 20 | 101 |
| 21 | 103 |
| 22 | 106 |
| 23 | 102 |
| 24 | 102 |
| 26 | 106 |
| 29 | 103 |
| 32 | 102 |
| 33 | 104 |

[Test Example 4] Heart Weight Lowering Effect of Compound of Example 1 in Heart Failure Animal Model In this Test Example, the heart weight lowering effect of the compound of Example 1 (referred to herein as "Example 1") was evaluated using CSQ-Tg mice as animal model for heart failure.

The Example 1 was suspended in 0.5% methylcellulose aqueous solution (hereinafter, in Test Examples, sometimes referred to as "vehicle") (10 mL/kg). The obtained suspension was orally administered to 5-week old female CSQ-Tg mice developing heart failure at a dose of 30 mg/kg bodyweight/day (n=7) or 90 mg/kg bodyweight/day (n=9) once daily (QD) for 21 days. For a negative control (vehicle administration group), 0.5% methylcellulose aqueous solution (n=7) was administered. Then, weights of the hearts were measured. The measurement of the weights was carried out by fractionating each of the hearts into four: left ventricle, right ventricle, left atrium, and right atrium. The sum of the weights of the four fractions was defined as the heart weight. The obtained heart weight was shown in Table 11, and the weight of each fraction was shown in Table 12.

TABLE 11

| (Mean ± standard deviation (mg)) | Vehicle administration group | Example 1 administration group (30 mg/kg bodyweight/ day) | Example 1 administration group (90 mg/kg bodyweight/ day) |
| --- | --- | --- | --- |
| Heart weight | 225.7 ± 14.3 | 202.8 ± 14.1** | 202.5 ± 19.1** |

**Williams' multiple comparison test ($p < 0.025$)

TABLE 12

| (Mean ± standard deviation (mg)) | Vehicle administration group | Example 1 administration group (30 mg/kg bodyweight/ day) | Example 1 administration group (90 mg/kg bodyweight/ day) |
| --- | --- | --- | --- |
| Left ventricle | 157.5 ± 16.3 | 147.4 ± 12.0 | 147.0 ± 8.6 |
| Right ventricle | 49.9 ± 3.1 | 41.8 ± 6.0** | 41.3 ± 7.6** |

TABLE 12-continued

| (Mean ± standard deviation (mg)) | Vehicle administration group | Example 1 administration group (30 mg/kg bodyweight/ day) | Example 1 administration group (90 mg/kg bodyweight/ day) |
|---|---|---|---|
| Left atrium | 11.4 ± 1.5 | 8.1 ± 3.8 | 9.1 ± 5.1 |
| Right atrium | 6.9 ± 1.4 | 5.5 ± 2.6 | 5.1 ± 2.2 |

**Williams' multiple comparison test (p < 0.025)

[Test Example 5] Effect of Example 1 on Survival Rate of Heart Failure Animal Model In this Test Example, effect of Example 1 on survival rate was examined using heart failure animal models. The mice reported in Larry R. Jones et al., J. Clin. Invest. 101: 1385-1393, 1998 were obtained from the University of Pennsylvania and bred in-house, which were cardiac-specific transgenic mice of Calsequestrin (CSQ) (CSQ-Tg mice) as the heart failure animal models. In the study, female mice were used, and dosing was started from the age of 5 weeks. The animals were fed with chow (CE-2, CLEA Japan, Inc.) and tap water under the condition of room temperature of 20 to 26° C., humidity of 40 to 70%, and lighting time of 12 hours/day (7:00 to 19:00). As already reported, in the CSQ-Tg mice, $Ca^{2+}$ intracellular release was suppressed, myocardial contraction was reduced, cardiac output was decreased, and cardiac hypertrophy and heart failure were developed.

To 5-week old female CSQ-Tg mice, Example 1 was orally administered at a dose of 10 mg/kg bodyweight/day or a dose of 30 mg/kg bodyweight/day in combination with candesartan cilexetil (1 mg/kg bodyweight/day) with a frequency of once daily (QD) for 68 days (n=18 in each case). To the control group, candesartan cilexetil (1 mg/kg bodyweight/day) was administered (n=18). The result was as shown in FIG. 1.

[Formulation Example 1] Manufacture of Capsules

| 1) Compound of Example 1 | 30 mg |
|---|---|
| 2) Cellulose fine powder | 10 mg |
| 3) Lactose | 19 mg |
| 4) Magnesium stearate | 1 mg |
| Total | 60 mg |

The ingredients 1), 2), 3) and 4) are mixed, and the obtained mixture is filled into gelatin capsules.

[Formulation Example 2] Manufacture of Tablets

| 1) Compound of Example 1 | 30 g |
|---|---|
| 2) Lactose | 50 g |
| 3) Corn starch | 15 g |
| 4) Carboxymethylcellulose calcium | 44 g |
| 5) Magnesium stearate | 1 g |
| 1000 Tablets Total | 140 g |

Each whole amount of the ingredients 1), 2), and 3) and 30 g of the ingredient 4) are kneaded with water, and the obtained mixture is dried in vacuo, and then subjected to particle sizing. To the obtained particles, 14 g of the ingredient 4) and 1 g of the ingredient 5) are mixed, and the obtained mixture is pressed by a tablet press. In this way, 1000 tablets each containing 30 mg of the compound of Example 1 are obtained.

INDUSTRIAL APPLICABILITY

The compound of the present invention has a calcium-sensing receptor antagonistic activity, and is expected to be useful as an agent for preventing or treating the diseases such as heart failure, or pulmonary hypertension.

The invention claimed is:
1. A compound represented by formula (I):

[Formula 1]

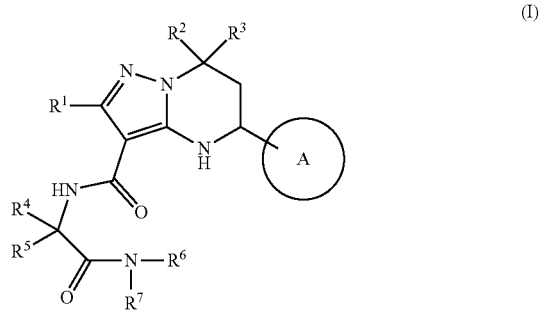

(I)

wherein
Ring A is a benzene ring;
$R^1$ is a hydrogen or a $C_{1-6}$ alkyl;
$R^2$ and $R^3$ are each independently a $C_{1-6}$ alkyl;
$R^4$ is a phenyl group which is optionally substituted with one to five $C_{1-6}$ alkyl groups;
$R^5$ is a $C_{1-6}$ alkyl;
$R^6$ is a hydrogen or a $C_{1-6}$ alkyl; and
$R^7$ is a hydrogen or a $C_{1-6}$ alkyl which is optionally substituted with one to three substituents selected from the group consisting of
 (a) a carbamoyl,
 (b) a carboxyl,
 (c) a hydroxy, and
 (d) a phenyl;
or a salt thereof.

2. The compound according to claim 1 or a salt thereof, wherein the compound is (5R)—N-((2R)-1-(((2S)-1-Amino-1-oxopropan-2-yl)amino)-2-(4-ethylphenyl)-1-oxobutan-2-yl)-2,7,7-trimethyl-5-phenyl-4,5,6,7-tetrahydropyrazolo[1,5-a]pyrimidine-3-carboxamide.

3. The compound according to claim 1 or a salt thereof, wherein the compound is (5R)—N-(1-(((2S)-1-Amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide.

4. The compound according to claim 1 or a salt thereof, wherein the compound is (5R)—N-(1-(((2S)-1-Amino-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide.

5. The compound according to claim 1 or a salt thereof, wherein the compound is (5R)—N-(1-(((2S)-1-Amino-3-methyl-1-oxobutan-2-yl)amino)-2-(4-ethylphenyl)-1- oxobutan-2-yl)-7,7-dimethyl-5-phenyl-4,5,6,7-tetrahydropyrazolo[1,5-a]pyrimidine-3-carboxamide.

6. A medicament comprising the compound or a salt thereof according to claim 1.

7. The medicament according to claim 6, wherein the medicament is an agent for treating heart failure, and wherein the compound is selected from the group consisting of:

- (5R)—N-((2R)-1-(((2S)-1-amino-1-oxopropan-2-yl)amino)-2-(4-ethylphenyl)-1-oxobutan-2-yl)-2,7,7-trimethyl-5-phenyl-4,5,6,7-tetrahydropyrazolo[1,5-a]pyrimidine-3-carboxamide;
- (5R)—N-(1-(((2S)-1-amino-1-oxopropan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide;
- (5R)—N-(1-(((2S)-1-Amino-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide; or
- (5R)—N-(1-(((2S)-1-Amino-3-methyl-1-oxobutan-2-yl)amino)-2-(4-ethylphenyl)-1-oxobutan-2-yl)-7,7-dimethyl-5-phenyl-4,5,6,7-tetrahydropyrazolo[1,5-a]pyrimidine-3-carboxamide.

\* \* \* \* \*